(12) United States Patent
Kahn et al.

(10) Patent No.: US 8,996,332 B2
(45) Date of Patent: Mar. 31, 2015

(54) PROGRAM SETTING ADJUSTMENTS BASED ON ACTIVITY IDENTIFICATION

(75) Inventors: Philippe Richard Kahn, Santa Cruz, CA (US); Arthur Kinsolving, Santa Cruz, CA (US); Mark Andrew Christensen, Santa Cruz, CA (US); Brian Y. Lee, Aptos, CA (US); David Vogel, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 904 days.

(21) Appl. No.: 12/490,304

(22) Filed: Jun. 23, 2009

(65) Prior Publication Data

US 2009/0319221 A1  Dec. 24, 2009

Related U.S. Application Data

(60) Provisional application No. 61/075,330, filed on Jun. 24, 2008.

(51) Int. Cl.
| | |
|---|---|
| G06F 19/00 | (2011.01) |
| G01P 15/00 | (2006.01) |
| A61B 5/11 | (2006.01) |
| A63B 24/00 | (2006.01) |
| G01C 22/00 | (2006.01) |

(52) U.S. Cl.
CPC ............... *G01P 15/00* (2013.01); *A61B 5/1123* (2013.01); *A63B 24/0062* (2013.01); *G01C 22/00* (2013.01); *A61B 2560/0209* (2013.01); *A61B 2562/0219* (2013.01); *A63B 2024/0071* (2013.01); *A63B 2220/17* (2013.01); *A63B 2220/44* (2013.01)

USPC .......................................... 702/141

(58) Field of Classification Search
CPC ....................................... G06F 3/017
USPC .......................................... 702/141
See application file for complete search history.

(56) References Cited

U.S. PATENT DOCUMENTS

| | | | |
|---|---|---|---|
| 4,285,041 A | 8/1981 | Smith | |
| 4,571,680 A | 2/1986 | Wu | |
| 4,578,769 A | 3/1986 | Frederick | |
| 4,700,369 A | 10/1987 | Seigal et al. | |
| 4,776,323 A | 10/1988 | Spector | |

(Continued)

FOREIGN PATENT DOCUMENTS

| | | |
|---|---|---|
| EP | 1 104 143 | 5/2001 |
| EP | 0 833 537 | 7/2002 |

(Continued)

OTHER PUBLICATIONS

PCT International Search Report and Written Opinion for PCT/US2009/48523, mailed Aug. 27, 2009, 8 pages.

(Continued)

*Primary Examiner* — Edward Raymond
(74) *Attorney, Agent, or Firm* — HIPLegal LLP; Judith A. Szepesi

(57) ABSTRACT

An electronic device monitors accelerations using an inertial sensor. The electronic device identifies a current motion state based on the accelerations. The electronic device determines an application that subscribes to a motion state identification service and notifies the application of the current motion state.

8 Claims, 16 Drawing Sheets

(56) References Cited

U.S. PATENT DOCUMENTS

| | | |
|---|---|---|
| 5,313,060 A | 5/1994 | Gast et al. |
| 5,386,210 A | 1/1995 | Lee |
| 5,430,480 A | 7/1995 | Allen et al. |
| 5,446,725 A | 8/1995 | Ishiwatari |
| 5,446,775 A | 8/1995 | Wright et al. |
| 5,454,114 A | 9/1995 | Yach et al. |
| 5,485,402 A | 1/1996 | Smith et al. |
| 5,506,987 A | 4/1996 | Abramson et al. |
| 5,515,419 A | 5/1996 | Sheffer |
| 5,583,776 A | 12/1996 | Levi et al. |
| 5,593,431 A | 1/1997 | Sheldon |
| 5,654,619 A | 8/1997 | Iwashita |
| 5,737,439 A | 4/1998 | Lapsley et al. |
| 5,771,001 A | 6/1998 | Cobb |
| 5,778,882 A | 7/1998 | Raymond et al. |
| 5,911,065 A | 6/1999 | Williams et al. |
| 5,955,667 A | 9/1999 | Fyfe |
| 5,960,085 A | 9/1999 | de la Huerga |
| 5,976,083 A | 11/1999 | Richardson et al. |
| 6,013,007 A | 1/2000 | Root et al. |
| 6,061,456 A | 5/2000 | Andrea et al. |
| 6,122,595 A | 9/2000 | Varley et al. |
| 6,129,686 A | 10/2000 | Friedman |
| 6,135,951 A | 10/2000 | Richardson et al. |
| 6,145,389 A | 11/2000 | Ebeling et al. |
| 6,246,321 B1 | 6/2001 | Rechsteiner et al. |
| 6,282,496 B1 | 8/2001 | Chowdhary |
| 6,353,449 B1 | 3/2002 | Gregg et al. |
| 6,369,794 B1 | 4/2002 | Sakurai et al. |
| 6,396,883 B2 | 5/2002 | Yang et al. |
| 6,408,330 B1 | 6/2002 | de la Huerga |
| 6,428,490 B1 | 8/2002 | Kramer et al. |
| 6,470,147 B1 | 10/2002 | Imada |
| 6,478,736 B1 | 11/2002 | Mault |
| 6,493,652 B1 | 12/2002 | Ohlenbusch et al. |
| 6,496,695 B1 | 12/2002 | Kouji et al. |
| 6,513,381 B2 | 2/2003 | Fyfe et al. |
| 6,522,266 B1 | 2/2003 | Soehren et al. |
| 6,532,419 B1 | 3/2003 | Begin et al. |
| 6,539,336 B1 | 3/2003 | Vock et al. |
| 6,595,929 B2 | 7/2003 | Stivoric et al. |
| 6,607,493 B2 | 8/2003 | Song |
| 6,611,789 B1 | 8/2003 | Darley |
| 6,628,898 B2 | 9/2003 | Endo |
| 6,634,992 B1 | 10/2003 | Ogawa |
| 6,665,802 B1 | 12/2003 | Ober |
| 6,672,991 B2 | 1/2004 | O'Malley |
| 6,685,480 B2 | 2/2004 | Nishimoto et al. |
| 6,700,499 B2 | 3/2004 | Kubo et al. |
| 6,731,958 B1 | 5/2004 | Shirai |
| 6,766,176 B1 | 7/2004 | Gupta et al. |
| 6,771,250 B1 | 8/2004 | Oh |
| 6,786,877 B2 | 9/2004 | Foxlin |
| 6,788,980 B1 | 9/2004 | Johnson |
| 6,790,178 B1 | 9/2004 | Mault et al. |
| 6,813,582 B2 | 11/2004 | Levi et al. |
| 6,823,036 B1 | 11/2004 | Chen |
| 6,826,477 B2 | 11/2004 | Ladetto et al. |
| 6,836,744 B1 | 12/2004 | Asphahani et al. |
| 6,881,191 B2 | 4/2005 | Oakley et al. |
| 6,885,971 B2 | 4/2005 | Vock et al. |
| 6,895,425 B1 | 5/2005 | Kadyk et al. |
| 6,898,550 B1 | 5/2005 | Blackadar et al. |
| 6,928,382 B2 | 8/2005 | Hong et al. |
| 6,941,239 B2 | 9/2005 | Unuma et al. |
| 6,959,259 B2 | 10/2005 | Vock et al. |
| 6,975,959 B2 | 12/2005 | Dietrich et al. |
| 7,002,553 B2 | 2/2006 | Shkolnikov |
| 7,010,332 B1 | 3/2006 | Irvin et al. |
| 7,020,487 B2 | 3/2006 | Kimata |
| 7,027,087 B2 | 4/2006 | Nozaki et al. |
| 7,028,547 B2 | 4/2006 | Shiratori et al. |
| 7,042,509 B2 | 5/2006 | Onuki |
| 7,054,784 B2 | 5/2006 | Flentov et al. |
| 7,057,551 B1 | 6/2006 | Vogt |
| 7,072,789 B2 | 7/2006 | Vock et al. |
| 7,092,846 B2 | 8/2006 | Vock et al. |
| 7,096,619 B2 | 8/2006 | Jackson et al. |
| 7,148,797 B2 | 12/2006 | Albert |
| 7,148,879 B2 | 12/2006 | Amento et al. |
| 7,149,964 B1 | 12/2006 | Cottrille et al. |
| 7,155,507 B2 | 12/2006 | Hirano et al. |
| 7,158,912 B2 | 1/2007 | Vock et al. |
| 7,169,084 B2 | 1/2007 | Tsuji |
| 7,171,222 B2 | 1/2007 | Fostick |
| 7,171,331 B2 | 1/2007 | Vock et al. |
| 7,173,604 B2 | 2/2007 | Marvit et al. |
| 7,176,886 B2 | 2/2007 | Marvit et al. |
| 7,176,887 B2 | 2/2007 | Marvit et al. |
| 7,176,888 B2 | 2/2007 | Marvit et al. |
| 7,177,684 B1 | 2/2007 | Kroll et al. |
| 7,180,500 B2 | 2/2007 | Marvit et al. |
| 7,180,501 B2 | 2/2007 | Marvit et al. |
| 7,180,502 B2 | 2/2007 | Marvit et al. |
| 7,200,517 B2 | 4/2007 | Darley et al. |
| 7,212,230 B2 | 5/2007 | Stavely |
| 7,212,943 B2 | 5/2007 | Aoshima et al. |
| 7,220,220 B2 | 5/2007 | Stubbs et al. |
| 7,245,725 B1 | 7/2007 | Beard |
| 7,254,516 B2 | 8/2007 | Case et al. |
| 7,280,096 B2 | 10/2007 | Marvit et al. |
| 7,280,849 B1 | 10/2007 | Bailey |
| 7,297,088 B2 | 11/2007 | Tsuji |
| 7,301,526 B2 | 11/2007 | Marvit et al. |
| 7,301,527 B2 | 11/2007 | Marvit et al. |
| 7,301,528 B2 | 11/2007 | Marvit et al. |
| 7,301,529 B2 | 11/2007 | Marvit et al. |
| 7,305,323 B2 | 12/2007 | Skvortsov et al. |
| 7,328,611 B2 | 2/2008 | Klees et al. |
| 7,334,472 B2 | 2/2008 | Seo et al. |
| 7,353,112 B2 | 4/2008 | Choi et al. |
| 7,365,735 B2 | 4/2008 | Reinhardt et al. |
| 7,365,736 B2 | 4/2008 | Marvit et al. |
| 7,365,737 B2 | 4/2008 | Marvit et al. |
| 7,379,999 B1 | 5/2008 | Zhou et al. |
| 7,387,611 B2 | 6/2008 | Inoue et al. |
| 7,397,357 B2 | 7/2008 | Krumm et al. |
| 7,451,056 B2 | 11/2008 | Flentov et al. |
| 7,457,719 B1 | 11/2008 | Kahn et al. |
| 7,457,872 B2 | 11/2008 | Aton et al. |
| 7,463,997 B2 | 12/2008 | Pasolini et al. |
| 7,467,060 B2 | 12/2008 | Kulach et al. |
| 7,489,937 B2 | 2/2009 | Chung et al. |
| 7,502,643 B2 | 3/2009 | Farringdon et al. |
| 7,512,515 B2 | 3/2009 | Vock et al. |
| 7,526,402 B2 | 4/2009 | Tenanhaus et al. |
| 7,608,050 B2 | 10/2009 | Shugg |
| 7,640,804 B2 | 1/2010 | Daumer et al. |
| 7,647,196 B2 | 1/2010 | Kahn et al. |
| 7,653,508 B1 | 1/2010 | Kahn et al. |
| 7,664,657 B1 | 2/2010 | Letzt et al. |
| 7,689,107 B2 | 3/2010 | Enomoto |
| 7,705,884 B2 | 4/2010 | Pinto et al. |
| 7,752,011 B2 | 7/2010 | Niva et al. |
| 7,753,861 B1 | 7/2010 | Kahn et al. |
| 7,765,553 B2 | 7/2010 | Douceur et al. |
| 7,774,156 B2 | 8/2010 | Niva et al. |
| 7,788,059 B1 | 8/2010 | Kahn et al. |
| 7,857,772 B2 | 12/2010 | Bouvier et al. |
| 7,881,902 B1 | 2/2011 | Kahn et al. |
| 7,892,080 B1 | 2/2011 | Dahl |
| 7,987,070 B2 | 7/2011 | Kahn et al. |
| 8,187,182 B2 | 5/2012 | Kahn et al. |
| 8,275,635 B2 | 9/2012 | Stivoric et al. |
| 8,398,546 B2 | 3/2013 | Pacione et al. |
| 2001/0047488 A1 | 11/2001 | Verplaetse et al. |
| 2002/0006284 A1 | 1/2002 | Kim |
| 2002/0023654 A1 | 2/2002 | Webb |
| 2002/0027164 A1 | 3/2002 | Mault et al. |
| 2002/0042830 A1 | 4/2002 | Bose et al. |
| 2002/0044634 A1 | 4/2002 | Rooke et al. |
| 2002/0054214 A1 | 5/2002 | Yoshikawa |
| 2002/0089425 A1 | 7/2002 | Kubo et al. |
| 2002/0109600 A1 | 8/2002 | Mault et al. |

(56) References Cited

U.S. PATENT DOCUMENTS

| | | |
|---|---|---|
| 2002/0118121 A1 | 8/2002 | Lehrman et al. |
| 2002/0122543 A1 | 9/2002 | Rowen |
| 2002/0138017 A1 | 9/2002 | Bui et al. |
| 2002/0142887 A1 | 10/2002 | O'Malley |
| 2002/0150302 A1 | 10/2002 | McCarthy et al. |
| 2002/0151810 A1 | 10/2002 | Wong et al. |
| 2002/0173295 A1 | 11/2002 | Nykanen et al. |
| 2002/0190947 A1 | 12/2002 | Feinstein |
| 2002/0193124 A1 | 12/2002 | Hamilton et al. |
| 2003/0018430 A1 | 1/2003 | Ladetto et al. |
| 2003/0033411 A1 | 2/2003 | Kavoori et al. |
| 2003/0048218 A1 | 3/2003 | Milnes et al. |
| 2003/0083596 A1 | 5/2003 | Kramer et al. |
| 2003/0093187 A1 | 5/2003 | Walker |
| 2003/0101260 A1 | 5/2003 | Dacier et al. |
| 2003/0109258 A1 | 6/2003 | Mantyjarvi et al. |
| 2003/0139692 A1 | 7/2003 | Barrey et al. |
| 2003/0139908 A1 | 7/2003 | Wegerich et al. |
| 2003/0149526 A1 | 8/2003 | Zhou et al. |
| 2003/0151672 A1 | 8/2003 | Robins et al. |
| 2003/0187683 A1 | 10/2003 | Kirchhoff et al. |
| 2003/0208110 A1 | 11/2003 | Mault et al. |
| 2003/0208113 A1 | 11/2003 | Mault et al. |
| 2003/0227487 A1 | 12/2003 | Hugh |
| 2003/0236625 A1 | 12/2003 | Brown et al. |
| 2004/0017300 A1 | 1/2004 | Kotzin et al. |
| 2004/0024846 A1 | 2/2004 | Randall et al. |
| 2004/0043760 A1 | 3/2004 | Rosenfeld et al. |
| 2004/0044493 A1 | 3/2004 | Coulthard |
| 2004/0047498 A1 | 3/2004 | Mulet-Parada et al. |
| 2004/0078219 A1 | 4/2004 | Kaylor et al. |
| 2004/0078220 A1 | 4/2004 | Jackson |
| 2004/0081441 A1 | 4/2004 | Sato et al. |
| 2004/0106421 A1 | 6/2004 | Tomiyoshi et al. |
| 2004/0106958 A1 | 6/2004 | Mathis et al. |
| 2004/0122294 A1 | 6/2004 | Hatlestad et al. |
| 2004/0122295 A1 | 6/2004 | Hatlestad et al. |
| 2004/0122296 A1 | 6/2004 | Hatlestad et al. |
| 2004/0122297 A1 | 6/2004 | Stahmann et al. |
| 2004/0122333 A1 | 6/2004 | Nissila |
| 2004/0122484 A1 | 6/2004 | Hatlestad et al. |
| 2004/0122485 A1 | 6/2004 | Stahmann et al. |
| 2004/0122486 A1 | 6/2004 | Stahmann et al. |
| 2004/0122487 A1 | 6/2004 | Hatlestad et al. |
| 2004/0125073 A1 | 7/2004 | Potter et al. |
| 2004/0130628 A1 | 7/2004 | Stavely |
| 2004/0135898 A1 | 7/2004 | Zador |
| 2004/0146048 A1 | 7/2004 | Cotte |
| 2004/0148340 A1 | 7/2004 | Cotte |
| 2004/0148341 A1 | 7/2004 | Cotte |
| 2004/0148342 A1 | 7/2004 | Cotte |
| 2004/0148351 A1 | 7/2004 | Cotte |
| 2004/0176067 A1 | 9/2004 | Lakhani et al. |
| 2004/0185821 A1 | 9/2004 | Yuasa |
| 2004/0219910 A1 | 11/2004 | Beckers |
| 2004/0225467 A1 | 11/2004 | Vock et al. |
| 2004/0236500 A1 | 11/2004 | Choi et al. |
| 2004/0242202 A1 | 12/2004 | Torvinen |
| 2004/0247030 A1 | 12/2004 | Wiethoff |
| 2004/0259494 A1 | 12/2004 | Mazar |
| 2005/0015768 A1 | 1/2005 | Moore |
| 2005/0027567 A1 | 2/2005 | Taha |
| 2005/0033200 A1 | 2/2005 | Soehren et al. |
| 2005/0038691 A1 | 2/2005 | Babu |
| 2005/0048955 A1 | 3/2005 | Ring |
| 2005/0078197 A1 | 4/2005 | Gonzales |
| 2005/0079873 A1 | 4/2005 | Caspi et al. |
| 2005/0101841 A9 | 5/2005 | Kaylor et al. |
| 2005/0102167 A1 | 5/2005 | Kapoor |
| 2005/0107944 A1 | 5/2005 | Hovestadt et al. |
| 2005/0113649 A1 | 5/2005 | Bergantino |
| 2005/0113650 A1 | 5/2005 | Pacione et al. |
| 2005/0131736 A1 | 6/2005 | Nelson et al. |
| 2005/0141522 A1 | 6/2005 | Kadar et al. |
| 2005/0143106 A1 | 6/2005 | Chan et al. |
| 2005/0146431 A1 | 7/2005 | Hastings et al. |
| 2005/0157181 A1 | 7/2005 | Kawahara et al. |
| 2005/0165719 A1 | 7/2005 | Greenspan et al. |
| 2005/0168587 A1 | 8/2005 | Sato et al. |
| 2005/0182824 A1 | 8/2005 | Cotte |
| 2005/0183086 A1 | 8/2005 | Abe et al. |
| 2005/0202934 A1 | 9/2005 | Olrik et al. |
| 2005/0203430 A1 | 9/2005 | Williams et al. |
| 2005/0210300 A1 | 9/2005 | Song et al. |
| 2005/0212751 A1 | 9/2005 | Marvit et al. |
| 2005/0212752 A1 | 9/2005 | Marvit et al. |
| 2005/0212753 A1 | 9/2005 | Marvit et al. |
| 2005/0212760 A1 | 9/2005 | Marvit et al. |
| 2005/0216403 A1 | 9/2005 | Tam et al. |
| 2005/0222801 A1 | 10/2005 | Wulff et al. |
| 2005/0232388 A1 | 10/2005 | Tsuji |
| 2005/0232404 A1 | 10/2005 | Gaskill |
| 2005/0234676 A1 | 10/2005 | Shibayama |
| 2005/0235058 A1 | 10/2005 | Rackus et al. |
| 2005/0238132 A1 | 10/2005 | Tsuji |
| 2005/0240375 A1 | 10/2005 | Sugai |
| 2005/0243178 A1 | 11/2005 | McConica |
| 2005/0245988 A1 | 11/2005 | Miesel |
| 2005/0248718 A1 | 11/2005 | Howell et al. |
| 2005/0256414 A1 | 11/2005 | Kettunen et al. |
| 2005/0258938 A1 | 11/2005 | Moulson |
| 2005/0262237 A1 | 11/2005 | Fulton et al. |
| 2005/0281289 A1 | 12/2005 | Huang et al. |
| 2006/0009243 A1 | 1/2006 | Dahan et al. |
| 2006/0017692 A1 | 1/2006 | Wehrenberg et al. |
| 2006/0020177 A1 | 1/2006 | Seo et al. |
| 2006/0029284 A1 | 2/2006 | Stewart |
| 2006/0063980 A1 | 3/2006 | Hwang et al. |
| 2006/0064276 A1 | 3/2006 | Ren et al. |
| 2006/0080551 A1 | 4/2006 | Mantyjarvi et al. |
| 2006/0090088 A1 | 4/2006 | Choi et al. |
| 2006/0090161 A1 | 4/2006 | Bodas et al. |
| 2006/0098097 A1 | 5/2006 | Wach et al. |
| 2006/0100546 A1 | 5/2006 | Silk |
| 2006/0109113 A1 | 5/2006 | Reyes et al. |
| 2006/0136173 A1 | 6/2006 | Case, Jr. et al. |
| 2006/0140422 A1 | 6/2006 | Zurek et al. |
| 2006/0149516 A1 | 7/2006 | Bond et al. |
| 2006/0154642 A1 | 7/2006 | Scannell, Jr. |
| 2006/0161377 A1 | 7/2006 | Rakkola et al. |
| 2006/0161459 A9 | 7/2006 | Rosenfeld et al. |
| 2006/0167387 A1 | 7/2006 | Buchholz et al. |
| 2006/0167647 A1 | 7/2006 | Krumm et al. |
| 2006/0167943 A1 | 7/2006 | Rosenberg |
| 2006/0172706 A1 | 8/2006 | Griffin et al. |
| 2006/0174685 A1 | 8/2006 | Skvortsov et al. |
| 2006/0201964 A1 | 9/2006 | DiPerna et al. |
| 2006/0204214 A1 | 9/2006 | Shah et al. |
| 2006/0205406 A1 | 9/2006 | Pekonen et al. |
| 2006/0206258 A1 | 9/2006 | Brooks |
| 2006/0223547 A1 | 10/2006 | Chin et al. |
| 2006/0249683 A1 | 11/2006 | Goldberg et al. |
| 2006/0256082 A1 | 11/2006 | Cho et al. |
| 2006/0257042 A1 | 11/2006 | Ofek et al. |
| 2006/0259268 A1 | 11/2006 | Vock et al. |
| 2006/0284979 A1 | 12/2006 | Clarkson |
| 2006/0288781 A1 | 12/2006 | Daumer et al. |
| 2006/0289819 A1 | 12/2006 | Parsons et al. |
| 2007/0004451 A1 | 1/2007 | C. Anderson |
| 2007/0005988 A1 | 1/2007 | Zhang et al. |
| 2007/0017136 A1 | 1/2007 | Mosher et al. |
| 2007/0024441 A1 | 2/2007 | Kahn et al. |
| 2007/0037605 A1 | 2/2007 | Logan et al. |
| 2007/0037610 A1 | 2/2007 | Logan |
| 2007/0038364 A1 | 2/2007 | Lee et al. |
| 2007/0040892 A1 | 2/2007 | Aoki et al. |
| 2007/0050157 A1 | 3/2007 | Kahn et al. |
| 2007/0060446 A1 | 3/2007 | Asukai et al. |
| 2007/0061105 A1 | 3/2007 | Darley et al. |
| 2007/0063850 A1 | 3/2007 | Devaul et al. |
| 2007/0067094 A1 | 3/2007 | Park et al. |
| 2007/0073482 A1 | 3/2007 | Churchill et al. |
| 2007/0075127 A1 | 4/2007 | Rosenberg |
| 2007/0075965 A1 | 4/2007 | Huppi et al. |

(56) References Cited

U.S. PATENT DOCUMENTS

| | | |
|---|---|---|
| 2007/0078324 A1 | 4/2007 | Wijisiriwardana |
| 2007/0082789 A1 | 4/2007 | Nissila et al. |
| 2007/0102525 A1 | 5/2007 | Orr et al. |
| 2007/0104479 A1 | 5/2007 | Machida |
| 2007/0106991 A1 | 5/2007 | Yoo |
| 2007/0125852 A1 | 6/2007 | Rosenberg |
| 2007/0130582 A1 | 6/2007 | Chang et al. |
| 2007/0142715 A1 | 6/2007 | Banet et al. |
| 2007/0143068 A1 | 6/2007 | Pasolini et al. |
| 2007/0145680 A1 | 6/2007 | Rosenberg |
| 2007/0150136 A1 | 6/2007 | Doll et al. |
| 2007/0156364 A1 | 7/2007 | Rothkopf |
| 2007/0161410 A1 | 7/2007 | Huang et al. |
| 2007/0165790 A1 | 7/2007 | Taori |
| 2007/0169126 A1 | 7/2007 | Todoroki et al. |
| 2007/0176898 A1 | 8/2007 | Suh |
| 2007/0192483 A1 | 8/2007 | Rezvani et al. |
| 2007/0195784 A1 | 8/2007 | Allen et al. |
| 2007/0204744 A1 | 9/2007 | Sako et al. |
| 2007/0208531 A1 | 9/2007 | Darley et al. |
| 2007/0208544 A1 | 9/2007 | Kulach et al. |
| 2007/0213085 A1 | 9/2007 | Fedora |
| 2007/0213126 A1 | 9/2007 | Deutsch et al. |
| 2007/0221045 A1 | 9/2007 | Terauchi et al. |
| 2007/0233788 A1 | 10/2007 | Bender |
| 2007/0239399 A1 | 10/2007 | Sheynblat et al. |
| 2007/0250261 A1 | 10/2007 | Soehren |
| 2007/0259685 A1 | 11/2007 | Engblom et al. |
| 2007/0259716 A1 | 11/2007 | Mattice et al. |
| 2007/0259717 A1 | 11/2007 | Mattice et al. |
| 2007/0260418 A1 | 11/2007 | Ladetto et al. |
| 2007/0260482 A1 | 11/2007 | Nurmela et al. |
| 2007/0263995 A1 | 11/2007 | Park et al. |
| 2007/0281762 A1 | 12/2007 | Barros et al. |
| 2007/0296696 A1 | 12/2007 | Nurmi |
| 2008/0005738 A1 | 1/2008 | Imai et al. |
| 2008/0030586 A1 | 2/2008 | Helbing et al. |
| 2008/0046888 A1 | 2/2008 | Appaji |
| 2008/0052716 A1 | 2/2008 | Theurer |
| 2008/0072014 A1 | 3/2008 | Krishnan et al. |
| 2008/0102785 A1 | 5/2008 | Childress et al. |
| 2008/0113689 A1 | 5/2008 | Bailey |
| 2008/0140338 A1 | 6/2008 | No et al. |
| 2008/0153671 A1 | 6/2008 | Ogg et al. |
| 2008/0161072 A1 | 7/2008 | Lide et al. |
| 2008/0165022 A1 | 7/2008 | Herz et al. |
| 2008/0168361 A1 | 7/2008 | Forstall et al. |
| 2008/0171918 A1 | 7/2008 | Teller et al. |
| 2008/0214358 A1 | 9/2008 | Ogg et al. |
| 2008/0231713 A1 | 9/2008 | Florea et al. |
| 2008/0231714 A1 | 9/2008 | Estevez et al. |
| 2008/0232604 A1 | 9/2008 | Dufresne et al. |
| 2008/0243432 A1 | 10/2008 | Kato et al. |
| 2008/0303681 A1 | 12/2008 | Herz et al. |
| 2008/0311929 A1 | 12/2008 | Carro et al. |
| 2009/0017880 A1 | 1/2009 | Moore et al. |
| 2009/0024233 A1 | 1/2009 | Shirai et al. |
| 2009/0031319 A1 | 1/2009 | Fecioru |
| 2009/0043531 A1 | 2/2009 | Kahn et al. |
| 2009/0047645 A1 | 2/2009 | Dibenedetto et al. |
| 2009/0067826 A1 | 3/2009 | Shinohara et al. |
| 2009/0082994 A1 | 3/2009 | Schuler et al. |
| 2009/0088204 A1 | 4/2009 | Culbert et al. |
| 2009/0098880 A1 | 4/2009 | Lindquist |
| 2009/0099668 A1 | 4/2009 | Lehman et al. |
| 2009/0124348 A1 | 5/2009 | Yoseloff et al. |
| 2009/0128448 A1 | 5/2009 | Riechel |
| 2009/0174782 A1 | 7/2009 | Kahn et al. |
| 2009/0213002 A1 | 8/2009 | Rani et al. |
| 2009/0234614 A1 | 9/2009 | Kahn et al. |
| 2009/0274317 A1 | 11/2009 | Kahn et al. |
| 2009/0296951 A1 | 12/2009 | De Haan |
| 2009/0325705 A1 | 12/2009 | Filer et al. |
| 2010/0056872 A1 | 3/2010 | Kahn et al. |
| 2010/0057398 A1 | 3/2010 | Darley et al. |
| 2010/0199189 A1 | 8/2010 | Ben-Aroya et al. |
| 2010/0245131 A1 | 9/2010 | Graumann |
| 2010/0277489 A1 | 11/2010 | Geisner et al. |
| 2010/0283742 A1 | 11/2010 | Lam |

FOREIGN PATENT DOCUMENTS

| | | |
|---|---|---|
| EP | 1271099 A2 | 1/2003 |
| GB | 2431813 A | 5/2007 |
| JP | 7020547 A | 1/1995 |
| JP | 2000-90069 | 3/2000 |
| JP | 2001-79699 | 3/2001 |
| JP | 2005-309691 A | 11/2005 |
| JP | 2006-026092 | 2/2006 |
| JP | 2006-118909 | 5/2006 |
| JP | 2006-239398 | 9/2006 |
| JP | 2007-075172 | 3/2007 |
| JP | 2007-080219 | 3/2007 |
| JP | 2007-142611 | 6/2007 |
| JP | 2007-206748 | 8/2007 |
| JP | 2007-215784 | 8/2007 |
| JP | 2007-226855 | 9/2007 |
| JP | 2008-173248 | 7/2008 |
| WO | WO 99/22338 | 5/1999 |
| WO | WO 00/63874 | 10/2000 |
| WO | WO 02/088926 | 11/2002 |
| WO | WO 2006/008790 | 1/2006 |
| WO | WO 2006/082809 | 8/2006 |

OTHER PUBLICATIONS

Bourzac, Katherine, "Wearable Health Reports," Technology Review, Feb. 28, 2006, 3 pages, http://www.techreview.com/printer_friendly_article_aspx?id+16431, accessed Mar. 22, 2007.

Cheng, et al., "Periodic Human Motion Description for Sports Video Databases", Proceedings of the Pattern Recognition (2004).

PCT/US2009/048523, International Preliminary Report on Patentability, mailing date Jan. 13, 2011, 7 pages.

Jones, L, et al, "Wireless Physiological Sensor System for Ambulatory Use," <http://ieeexplore.ieee.org/xpl/freeabs_all.jsp?tp=&arnumber=1612917&isnumber=33861>, Apr. 3-5, 2006.

"Sensor Fusion," <www.u-dynamics.com>, accessed Aug. 29, 2008, 2 pages.

Wang, Shu, et al, "Location Based Services for Mobiles: Technologies and Standards, LG Electronics MobileComm," IEEE ICC 2008, Beijing, pp. 1-66 (part 1 of 3).

Wang, Shu, et al, "Location Based Services for Mobiles: Technologies and Standards, LG Electronics MobileComm," IEEE ICC 2008, Beijing, pp. 67-92 (part 2 of 3).

Wang, Shu, et al, "Location Based Services for Mobiles: Technologies and Standards, LG Electronics MobileComm," IEEE ICC 2008, Beijing, pp. 93-123 (part 3 of 3).

Weckesser, P, et al, "Multiple Sensorprocessing for High-Precision Navigation and Environmental Modeling with a Mobile Robot," IEEE, 1995, pp. 453-458.

Yoo, Chang-Sun, et al, "Low Cost GPS/INS Sensor Fusion System for UAV Navigation," IEEE, 2003, 9 pages.

Anderson, Ian, et al, "Shakra: Tracking and Sharing Daily Activity Levels with Unaugmented Mobile Phones," Mobile Netw Appl, Aug. 3, 2007, pp. 185-199.

Aylward, Ryan, et al, "Sensemble: A Wireless, Compact, Multi-User Sensor System for Interactive Dance," International Conference on New Interfaces for Musical Expression (NIME06), Jun. 4-8, 2006, pp. 134-139.

Baca, Arnold, et al, "Rapid Feedback Systems for Elite Sports Training," IEEE Pervasive Computing, Oct.-Dec. 2006, pp. 70-76.

Bakhru, Kesh, "A Seamless Tracking Solution for Indoor and Outdoor Position Location," IEEE 16th International Symposium on Personal, Indoor, and Mobile Radio Communications, 2005, pp. 2029-2033.

Bliley, Kara E, et al, "A Miniaturized Low Power Personal Motion Analysis Logger Utilizing MEMS Accelerometers and Low Power Microcontroller," IEEE EMBS Special Topic Conference on Microtechnologies in Medicine and Biology, May 12-15, 2005, pp. 92-93.

(56) References Cited

OTHER PUBLICATIONS

Fang, Lei, et al, "Design of a Wireless Assisted Pedestrian Dead Reckoning System—The NavMote Experience," IEEE Transactions on Instrumentation and Measurement, vol. 54, No. 6, Dec. 2005, pp. 2342-2358.
Healey, Jennifer, et al, "Wearable Wellness Monitoring Using ECG and Accelerometer Data," IEEE Int. Symposium on Wearable Computers (ISWC'05), 2005, 2 pages.
Hemmes, Jeffrey, et al, "Lessons Learned Building TeamTrak: An Urban/Outdoor Mobile Testbed," 2007 IEEE Int. Conf. on Wireless Algorithms, Aug. 1-3, 2007, pp. 219-224.
Jovanov, Emil, et al, "A Wireless Body Area Network of Intelligent Motion Sensors for Computer Assisted Physical Rehabilitation," Journal of NeuroEngineering and Rehabilitation, Mar. 2005, 10 pages.
Kalpaxis, Alex, "Wireless Temporal-Spatial Human Mobility Analysis Using Real-Time Three Dimensional Acceleration Data," IEEE Intl. Multi-Conf. on Computing in Global IT (ICCGI'07), 2007, 7 pages.
Milenkovic, Milena, et al, "An Accelerometer-Based Physical Rehabilitation System," IEEE SouthEastern Symposium on System Theory, 2002, pp. 57-60.
Otto, Chris, et al, "System Architecture of a Wireless Body Area Sensor Network for Ubiquitous Health Monitoring," Journal of Mobile Multimedia, vol. 1, No. 4, 2006, pp. 307-326.
Park, Chulsung, et al, "Eco: An Ultra-Compact Low-Power Wireless Sensor Node for Real-Time Motion Monitoring," IEEE Int. Symp. on Information Processing in Sensor Networks, 2005, pp. 398-403.
Shen, Chien-Lung, et al, "Wearable Band Using a Fabric-Based Sensor for Exercise ECG Monitoring," IEEE Int. Symp. on Wearable Computers, 2006, 2 pages.
Tapia, Emmanuel Munguia, et al, "Real-Time Recognition of Physical Activities and Their Intensities Using Wireless Accelerometers and a Heart Rate Monitor," IEEE Cont. on Wearable Computers, Oct. 2007, 4 pages.
Wixted, Andrew J, et al, "Measurement of Energy Expenditure in Elite Athletes Using MEMS-Based Triaxial Accelerometers," IEEE Sensors Journal, vol. 7, No. 4, Apr. 2007, pp. 481-488.
Wu, Winston H, et al, "Context-Aware Sensing of Physiological Signals," IEEE Int. Conf. on Engineering for Medicine and Biology, Aug. 23-26, 2007, pp. 5271-5275.
"Access and Terminals (AT); Multimedia Message Service (MMS) for PSTN/ISDN; Multimedia Message Communication Between a Fixed Network Multimedia Message Terminal Equipment and a Multimedia Message Service Centre," ETSI AT-F Rapporteur Meeting, Feb. 4-6, 2003, Gothenburg, DES/AT-030023 V0.0.1 (Mar. 2003).
Ang, Wei Tech, et al, "Zero Phase Filtering for Active Compensation of Period Physiological Motion," Proc 1st IEEE / RAS-EMBS International Conference on Biomedical Robotics and Biomechatronics, Feb. 20-22, 2006, pp. 182-187.
"Decrease Processor Power Consumption using a CoolRunner CPLD," Xilinx XAPP347 (v1.0), May 16, 2001, 9 pages.
Lee, Hyunseok, et al, A Dual Processor Solution for the MAC Layer of a Software Defined Radio Terminal, Advanced Computer Architecture Laboratory, University of Michigan, 25 pages.
Ricoh, "Advanced digital technology changes creativity," <http://www.ricoh.com/r_dc/gx/gx200/features2.html>, Accessed May 12, 2011, 4 pages.
Tech, Ang Wei, "Real-time Image Stabilizer," <http://www.mae.ntu.edu.sg/ABOUTMAE/DIVISIONS/RRC_BIOROBOTICS/Pages/rtimage.aspx>, Mar. 23, 2009, 3 pages.
Weinberg, Harvey, "Minimizing Power Consumption of iMEMS® Accelerometers," Analog Devices, <http://www.analog.com/static/imported-files/application_notes/5935151853362884599AN601.pdf>, 2002, 5 pages.
Dao, Ricardo, "Inclination Sensing with Thermal Accelerometers", MEMSIC, May 2002, 3 pages.
Lee, Seon-Woo, et al., "Recognition of Walking Behaviors for Pedestrian Navigation," ATR Media Integration & Communications Research Laboratories, Kyoto, Japan, 4 pages.
Mizell, David, "Using Gravity to Estimate Accelerometer Orientation", Seventh IEEE International Symposium on Wearable Computers, 2003, 2 pages.
Ormoneit, D., et al., "Learning and Tracking Cyclic Human Motion," 7 pages.
Weinberg, Harvey, "MEMS Motion Sensors Boost Handset Reliability" Jun. 2006, http://www.mwrf.com/Articles/Print.cfm?ArticleID=12740, Feb. 21, 2007, 4 pages.
Margaria, Rodolfo, "Biomechanics and Energetics of Muscular Exercise", Chapter 3, pp. 105-125, Oxford: Clarendon Press 1976.
EP 09798529.5, Extended European Search Report, Dated Jan. 8, 2014, 5 pages.
EP 09798529.5, Extended European Search Report, Dated Nov. 8, 2014, 5 pages.
"Heart Rate Monitor Sports Bra," <www.numetrex.com/about/heart-rate-monitor-sports-bra>, Accessed Aug. 9, 2013, 2 pages.
Meinhold, Bridgette, "Adidas by Stella McCartney's Tennis Bra Includes Built-In Heart Sensor," <www.ecouterre.com/adidas-by-stella-mccartneys-tennis-bra-includes-built-in-heart-sensor/>, Mar. 23, 2012, 2 pages.
"Smart Underwear With Biosensors Availability in the Market Kudos to Modern Inkjet Printer Technology," Accessed Aug. 9, 2013, 2 pages.
Japanese Patent Application No. 2011-516623, Final Office Action mailed Apr. 15, 2014, 6 pages.
Japanese Patent Application No. 2011-516623, Office Action mailed Oct. 31, 2013, 9 pages.

PROGRAM SETTING ADJUSTMENTS BASED ON ACTIVITY IDENTIFICATION

RELATED APPLICATIONS

This patent application claims the benefit under 35 U.S.C. §119(e) of U.S. Provisional Application No. 61/075,330, filed Jun. 24, 2008, which is herein incorporated by reference.

FIELD OF THE INVENTION

This invention relates to a method of monitoring human activity, and more particularly to identifying user motion states and adjusting program settings based on the user motion state.

BACKGROUND

The development of Micro-Electro-Mechanical Systems (MEMS) technology has enabled manufacturers to produce inertial sensors (e.g., accelerometers) of sufficiently small size, cost, and power consumption to fit into portable electronic devices. Such inertial sensors can be found in a limited number of commercial electronic devices such as cellular phones, portable music players, pedometers, game controllers, and portable computers.

Step counting devices (e.g., pedometers) are used to monitor an individual's daily activity by keeping track of the number of steps that he or she takes. Steps are counted by sensing accelerations caused by user motion. Step counting devices are not able to detect or count motions other than steps. Nor are step counting devices capable of differentiating between different user activities.

Some step counting devices may be attached to and receive input from external sensors (e.g., a bike cadence sensor) to detect a motion other than a step. However, such step counting devices rely on external sensors for such monitoring capability. These devices are not capable of detecting or counting motions other than steps without the input from external sensors.

BRIEF DESCRIPTION OF THE DRAWINGS

The present invention is illustrated by way of example, and not by way of limitation, and can be more fully understood with reference to the following detailed description when considered in connection with the following figures.

DETAILED DESCRIPTION

Embodiments of the present invention are designed to monitor a user's motion state using an inertial sensor. In one embodiment, accelerations are monitored, and a current user motion state is identified from multiple recognizable user motion states based on the accelerations. These motion states include any activities based on periodic human motions, including, for example: walking, running, inline skating, bicycling, exercising on an elliptical machine, exercising on a rowing machine, and cross country skiing, as well as other types of motions such as riding in a car, on a train, on an escalator, etc. In one embodiment, periodic human motions that are appropriate to the current user activity are counted. In one embodiment, the system provides user data on each of the activities that were performed. In this way, a user can monitor his or her overall activity level throughout the day, as well individual activities.

Figure 1:
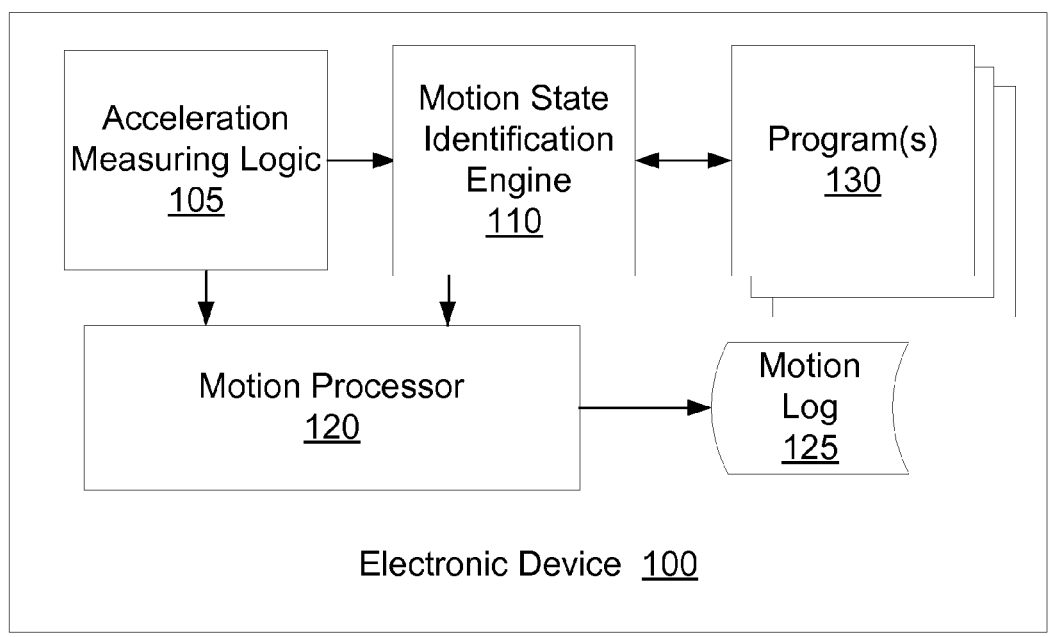
FIG. 1 is a block diagram illustrating an electronic device, in accordance with one embodiment of the present invention.

FIG. 1 is a block diagram illustrating a particular machine or electronic apparatus 100, in accordance with one embodiment of the present invention. In one embodiment, the electronic device 100 is a portable electronic device that includes one or more inertial sensors. The inertial sensors may measure accelerations along a single axis or multiple axes. The inertial sensors may measure linear as well as rotational (angular) accelerations. In one embodiment, the inertial sensors may be two axis or three axis accelerometers. In one embodiment, the inertial sensors may be gyroscopes, or other sensors.

The electronic device 100 may be used to identify user motion states and count periodic human motions appropriate to identified user activities. In one embodiment, electronic device 100 operates in conjunction with a server (not shown) to identify user motion states and count periodic human motions. In one embodiment, periodic human motions may be accurately counted regardless of the placement and/or orientation of the device 100 on a user. For example, the electronic device 100 may be carried in a backpack, pocket, purse, hand, or elsewhere, and accurate motion state may be identified. Furthermore, the periodic human motions may still be accurately counted. In one embodiment, the device 100 is optimally placed in a particular one of multiple locations on a human for a particular type of motion, to facilitate detection of user motion state and counting of periodic motions. For example, the electronic device 100 may be optimally placed in a pocket while bicycling to ensure the greatest accuracy in counting pedal motions. However, the electronic device 100 may be placed elsewhere and still correctly detect user motion state and count periodic motions. Periodic human motions may be accurately counted whether the electronic device 100 maintains a fixed orientation or changes orientation during use.

The electronic device 100 in one embodiment comprises an acceleration measuring logic 105, a motion state identification engine 110, a motion processor 120, and a motion log 125. The acceleration measuring logic 105 may be an inertial sensor or other acceleration sensitive instrument. The acceleration measuring logic 105 may continuously take measurements of acceleration data. The measurements of acceleration data are taken at a sampling rate that may be fixed or variable. In one embodiment, the acceleration measuring logic 105 receives a timing signal from a timer (not shown) in order to take measurements at the sampling rate. In one embodiment, the acceleration measuring logic 105 is coupled to the activity identification engine 110 and to the motion processor 120, and acceleration measurement data is sent to the activity identification engine 110 and to the motion processor 120 for processing.

In one embodiment, measurement data is processed by the motion state identification engine 110 to identify a user's motion state. The motion state identification engine 110 uses the motion data to identify the user motion state from a plurality of identifiable motion states. The motion state identification engine 110 may identify a motion state by monitoring for different events, each event indicative of a type of motion state. In one embodiment, when enough events indicative of a particular motion state are detected without contraindication, the motion state identification engine 110 notifies the motion processor 120 that the user is in the identified motion state. For example, if a number of running steps are detected, without intervening stops or other motion types, the motion state identification engine 110 identifies the user as being in a running motion state.

The motion processor 120 may process acceleration measurement data to detect periodic human motions. In one embodiment, a series of motion criteria are applied to the acceleration measurement data. If each of the motion criteria is satisfied, a periodic human motion may be identified, and counted. In one embodiment, a different set of motion criteria may apply for each user activity. In one embodiment, criteria may include positive criteria (ones that must be met to classify a motion in a certain way) and negative criteria (ones that cannot be met to classify a motion in a certain way). Once the motion state identification engine 110 has identified a user activity, the motion processor 120 may apply the set of motion criteria specific to the identified activity to detect appropriate periodic human motions for that activity. When an appropriate periodic human motion is detected, it may be recorded in the motion log 125. In one embodiment, the method described in U.S. patent application Ser. No. 12/069,267, entitled "Human Activity Monitoring Device With Activity Identification," filed on Feb. 8, 2008, is utilized to identify activities. That application is herein incorporated by reference.

If no motion state has been identified by the motion state identification engine 110, in one embodiment possible periodic human motions are buffered by the motion processor 120 in a memory (not shown). Once the motion state identification engine 110 identifies the user motion state, these buffered periodic human motions may be recorded in the motion log 125 as periodic human motions appropriate to the identified user motion state. For example, if the user starts to jog, the first few step counts may be buffered to ensure that the system identifies jogging. Once the user's motion state—jogging—is positively identified, the buffered step counts are added to the step counter. This ensures that even if positive identification of the user motion state takes time, activity performed during the identification period is still tracked.

The motion log 125 may maintain separate data sets for each type of periodic human motion. For example, the motion log 125 may have a first record of the number of steps walked in a day and a second record of the number of strides a user has inline skated in a day. The motion log 125 may also include additional statistics for different periodic human motions, for example the average walking speed, the length of time and time in a day during which a particular activity was performed, etc. In one embodiment, the user may be provided with a total activity level evaluation as well, based on the various activities performed.

In one embodiment, the electronic device 100 includes one or more programs or modules 130, which may include applications, system managers, etc. The applications may include applications that use acceleration measurement data (e.g., a pedometer application, a gesture recognition application, a motion sensitive game, etc.) and/or applications that do not directly use acceleration measurement data (e.g., a telephony application, a music player application, a video application, etc.). The system managers may include power managers, screen controllers, volume controllers, and other systems. The programs 130 may receive an identification of a current user motion state from the motion state identification engine 110. In one embodiment, a program 130 receives an identification of a current user motion state when the program is initially activated. In one embodiment, the program 130 receives user motion state updates periodically (e.g., once every second, once every 10 seconds, once every minute, etc.) or continuously. In one embodiment, the program 130 receives a user motion state update when the motion state changes. The program 130 may then modify one or more settings based on the motion state.

Figure 2:
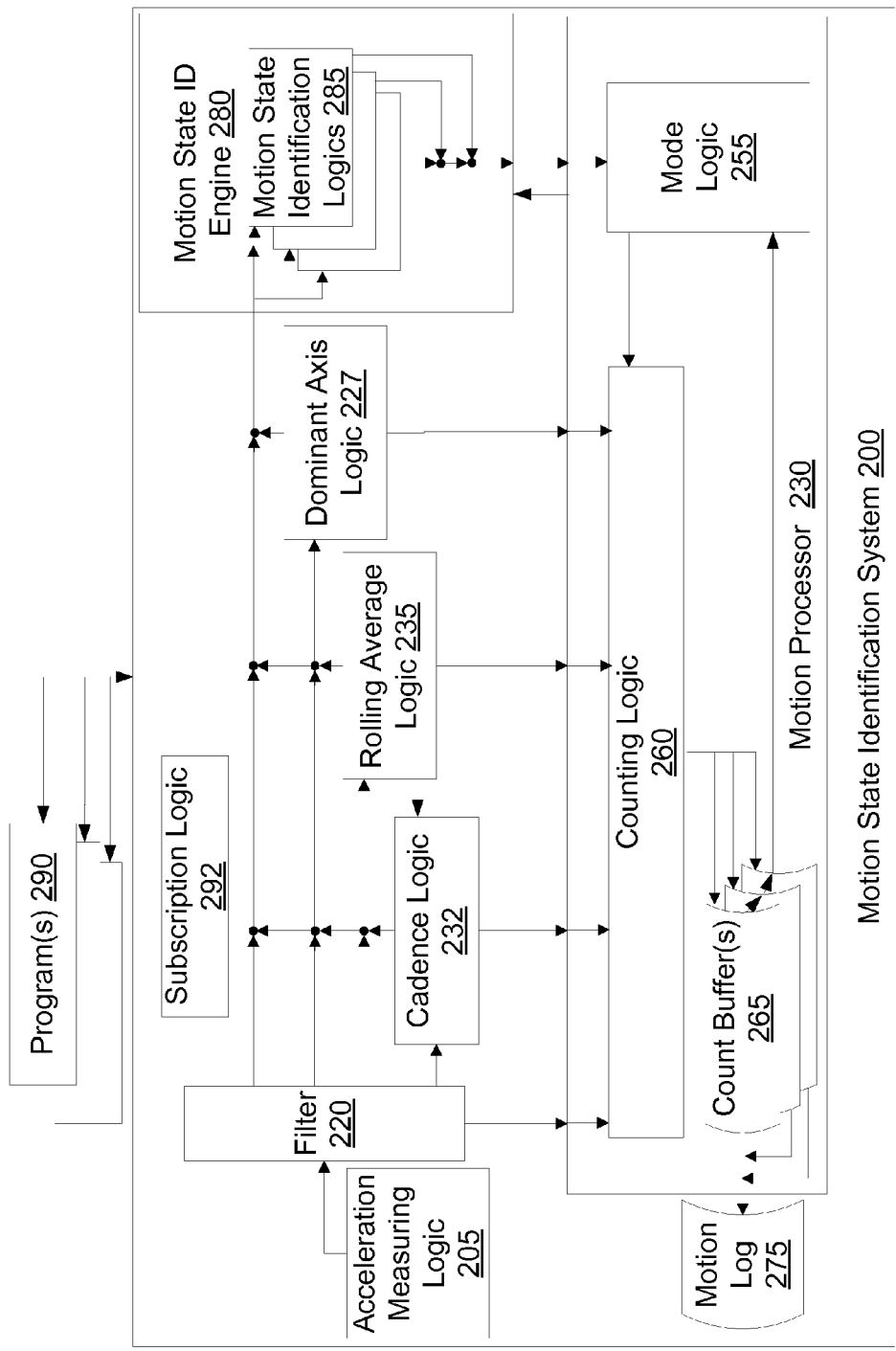
FIG. 2 is a block diagram illustrating a motion identification system, in accordance with one embodiment of the present invention.

FIG. 2 is a block diagram illustrating a motion state identification system 200, in accordance with one embodiment of the present invention. The motion state identification system 200 in one embodiment includes an electronic device. In one embodiment, the electronic device is a portable electronic device that includes one or more inertial sensors. In another embodiment, the motion state identification system 200 includes an electronic device coupled to a server. The distribution of the functionality between the portable device and the server may vary. In one embodiment, data acquisition is handled by the portable device, while the server and the portable device share processing of the data. In one embodiment, temporary data storage is handled by the portable device, but historical data is stored on the server. In one embodiment, the motion state identification system 200 comprises a filter 220, a cadence logic 232, a rolling average logic 235, a dominant axis logic 227, a motion state identification engine 280, a motion processor 230 and a motion log 275.

The acceleration measuring logic 205 may be an inertial sensor or other acceleration sensitive instrument. The acceleration measuring logic 205 may continuously take measurements of acceleration data at a sampling rate that may be fixed or variable. In one embodiment, the acceleration measuring logic 205 receives a timing signal from a timer (not shown) in order to take measurements at the sampling rate. In one embodiment, the acceleration measuring logic 205 is a 3-dimensional accelerometer. In one embodiment, the sampling rate of the acceleration measuring logic 205 may be based on a level of activity detected. In one embodiment, for slower motions, the sampling rate is decreased.

In one embodiment, the acceleration measuring logic 205 is coupled to the filter 220. Measurement data may be processed by the filter 220 to remove noise. The filter 220 may be implemented in hardware, software, or both hardware and software. In one embodiment, the filter 220 includes multiple filters, and a determination of which filters to apply to the measurement data is made based upon the type of user activity detected. For example, a low pass filter may be used to remove high frequency noise that would interfere with step counting when a user is walking. In contrast, a high pass filter may be used when quick motions are to be monitored. The filters may, in one embodiment, include one or more of high pass filters, low pass filters, bandpass filters, and band gap filters. In one embodiment, the filters have adjustable frequency ranges. In one embodiment, one or more filters may be applied to different data sets. For example, a low pass filter may be used to remove jitter data from the inertial data, while the user is jogging. At the same time, in one embodiment, a low pass filter may be applied to the audio stream being played to the user.

Many types of motions that are useful to keep track of have a periodic set of movements. Specific periodic human motions may be characteristic of different types of user activity. For example, to walk, an individual must lift a first leg, move it forward, plant it, and then repeat the same series of motions with a second leg. In contrast, a person inline skating performs a repeated sequence of pushing, coasting and liftoff for each leg. For a particular individual, the sequence of walking motions will usually occur in about the same amount of time, and the sequence of skating motions will usually occur in about the same amount of time. The repeated set of motions can be considered a unit, and defines a motion cycle. The amount of time that it takes to complete one motion cycle defines the motion cycle's period, and the number of motion cycles that occur in a given unit of time define the motion cycle's frequency, or cadence.

In one embodiment, filtered measurement data may be passed on to the cadence logic 232. The cadence logic 232 may determine a period and/or cadence of a motion cycle. The period and/or cadence of the motion cycle are based upon user activity (e.g. inline skating, biking, running, walking, etc). In one embodiment, the motion cycle's period is verified or updated after each periodic human motion. The current motion cycle period in one embodiment is a rolling average of the motion cycle periods, based on a recent set of motions of the same activity type. This rolling average data may be received from the rolling average logic 235, as discussed in more detail below.

In one embodiment, the cadence logic 232 maintains one or more cadence windows. A cadence window is a window of time since a last periodic human motion was counted that is looked at to detect a new periodic human motion. When motion criteria (e.g., threshold conditions) are met within a cadence window, a periodic human motion is detected, whereas when motion criteria are met outside of the cadence windows no periodic human motion is detected. A cadence window may be used to facilitate accurate measurement of a periodic human motion (e.g., a step, inline skating stride, bicycle pedal, rowing stroke, etc.).

A cadence window may be set based on the period and/or cadence of the actual motion cycle (e.g., a stepping period), on set limits, and/or on other factors. In one embodiment, the cadence window is determined by using the period of the current periodic human motion. In one embodiment, the cadence window may be a multiple of the current period (e.g. if the user is jogging at 180 steps per minute, e.g. three steps per second, the cadence window may be 0.66 seconds, e.g. twice the expected period between steps). In one embodiment, the cadence window is a dynamic cadence window that continuously updates as a user's cadence changes during a particular activity. For example, using a dynamic cadence window, the cadence window length may be verified or adjusted after each periodic human motion. If no previous periodic human motions have been detected, or if less than a set number of periodic human motions to determine a dynamic cadence window have been detected, a default cadence window may be used. Once enough periodic human motions have been detected to determine a dynamic motion cycle cadence or period, the cadence window may be set to the determined motion cycle period plus or minus an error factor. In one embodiment, a count of between about two to about ten periodic human motions is sufficient to set a dynamic cadence window.

In one embodiment, a separate default cadence window may be maintained for each identifiable user activity. In one embodiment, a separate default cadence window may be maintained for each user, for each identifiable user activity. Each identifiable user activity may have, for example, a unique default cadence window. When no specific current user activity has yet been identified, these separate cadence windows may be maintained concurrently for each of the possible user activities, in order to correctly identify the actual user motion state. Periodic human motions that occur outside of a default cadence window may indicate that the user motion state has changed.

Once the motion cycle's period is detected, the cadence logic 232 may set one or more sample periods for the rolling average logic 235 to use based upon the motion cycle's period. A sample period can include a specified time frame over which obtained measurements are used to perform a calculation. In one embodiment, the sample period(s) is approximately the length of the motion cycle's period. In one embodiment, a sample period is set such that it is a multiple of the motion cycle's period.

In one embodiment, the rolling average logic 235 may receive filtered measurement data from the filter 220 and one or more sample periods from the cadence logic 232. The rolling average logic 235 creates one or more rolling averages of accelerations as measured by the inertial sensor(s) over the sample period(s) set by the cadence logic 232. The rolling averages of accelerations may be used for determining an orientation of the electronic device, for determining thresholds to compare acceleration measurements against, and/or for other purposes. In one embodiment, the rolling average logic 235 creates one or more rolling averages of accelerations for determining an orientation of the electronic device 200, at least one rolling average having a period that is at least the motion cycle's period. In one embodiment, the rolling average logic 235 creates a rolling average of accelerations for determining a lower threshold to compare acceleration measurements against, the rolling average having a sample period that is at least twice the stepping period.

The rolling average logic 235 may create one or more rolling averages of data other than accelerations. In one embodiment, the rolling average logic 235 creates a rolling average of motion cycle periods, where the rolling average is the rolling average of the periodic human motions. In one embodiment, the rolling average of motion cycle periods is calculated over the past four counted periodic human motions. The rolling average of the motion cycle periods may be used by the cadence logic 232 to dynamically determine a cadence window and a current motion cycle cadence.

In one embodiment, rolling averages may be maintained in memory registries that keep track of rolling average values and the number of samples that were used to calculate current rolling average values. When a new measurement is taken, it can be incorporated into the rolling average value, and the registry can than be updated with a new rolling average value. Alternatively, the rolling averages may be maintained by buffering the measurements used to calculate the rolling averages. In one embodiment FIFO buffers may be used, such that as the buffers fill, oldest measurement data is discarded and replaced by new measurement data. The measurements in the buffer can be averaged after each measurement to determine a new rolling average.

In one embodiment, the dominant axis logic 227 receives at least filtered acceleration data from the filter 220, and rolling averages of accelerations from the rolling average logic 235. In one embodiment, the dominant axis logic 227 receives only rolling averages of accelerations from the rolling average logic 235. The dominant axis logic 227 may assign a dominant axis based on the received information.

In one embodiment, the dominant axis logic 227 determines an orientation of the electronic device and/or the inertial sensor(s) within the motion identification system 200. The orientation may be determined based upon the rolling averages of accelerations created by the rolling average logic 235. In one embodiment, once the orientation is determined, a dominant axis is assigned based upon the orientation. Determining an orientation of the electronic device may include identifying a gravitational influence. The axis with the largest absolute rolling average may be the axis most influenced by gravity, which may change over time (e.g. as the electronic device is rotated). Therefore, a new dominant axis may be assigned when the orientation of the electronic device and/or the inertial sensor(s) attached to or embedded in the electronic device changes.

In one embodiment, the axis with the largest absolute rolling average over the sample period is assigned as the dominant axis. In one embodiment, the dominant axis does not correspond to one of the actual axes of the inertial sensor(s) in a current orientation, but rather to an axis that is defined as approximately aligned to gravity. In one embodiment, the dominant axis corresponds to a virtual axis that is a component of a virtual coordinate system. In one embodiment, the dominant axis setting logic 240 assigns the dominant axis by performing a true gravity assessment, such as by doing trigonometric calculations on the actual axes based on the gravitational influence. In one embodiment, the dominant axis setting logic 240 assigns the dominant axis by comparing the gravitational influence to a data structure such as a lookup table, associative array, hash table, adjacency matrix, etc.

In one embodiment, the dominant axis is determined based on criteria other than a device orientation in relation to gravity. For example, the dominant axis may be determined based on an axis that has a greatest peak to peak variation within a motion cycle. In one embodiment, multiple dominant axes are assigned, each dominant axis being associated with a different user activity. The dominant axis may be assigned based on criteria specific to an associated user activity. For example, a first dominant axis may be assigned to the user activity of walking based on an axis that is most influenced by gravity, and a second dominant axis may be assigned to the user activity of bicycling based on an axis that has the greatest peak to peak variance.

The motion state identification engine 280 may receive as an input filtered acceleration measurement data from the filter 220. The motion state identification engine 280 may also receive a cadence and/or period of a current motion cycle and a current cadence window from the cadence logic 232, rolling averages (e.g., of accelerations) from the rolling average logic 235, and one or more dominant axes from the dominant axis logic 227.

In one embodiment, the motion state identification engine 280 includes multiple motion state identification logics 285. In one embodiment, each of the motion state identification logics 285 is set up to determine whether the current acceleration data defines a particular activity, movement, or other type of motion state. Alternatively, motion state identification logic 285 may be capable of identifying two or more possible motion states. In one embodiment, the motion state identification engine 280 includes only a single motion state identification logic 285, which is used to identify all identifiable user motion states. Alternatively, there may be separate motion state identification logic 285 for each activity, there may be separate motion state identification logics 285 for each activity type, or there may be separate motion state identification logics 285 based on some other criteria. In one embodiment, there is a separate motion state identification logic 285 for motion states associated with periodic human motion (e.g. walking, running, bicycling, etc.) and motion states not associated with such motions (e.g. riding in a car, escalator, elevator, etc.)

Motion state identification logic 285 identifies a specific user motion state by monitoring for acceleration data indicative of that type of motion state. The acceleration data is analyzed, and the motion state identification logic 285 may make its determination based on one or more of the received acceleration data, motion cycle cadence, motion cycle period, cadence windows, rolling averages, and dominant axes. In one embodiment, when enough events indicative of a particular user motion state are detected by motion state identification logic 285, the motion state identification engine 280 notifies the motion processor 230 that the user is in the identified motion state. In one embodiment, each time motion state identification logic 285 detects an event indicative of a particular type of motion, that event is forwarded to the motion processor 230. The motion processor 230 may then determine whether the user is performing an activity associated with the received event or received events. In one embodiment, the motion state identification logic 285 also monitor for negative events that indicate that a user is not performing a particular user activity, or is not in a particular motion state. These negative events may also be used by the motion state identification engine 280 and/or the motion processor 230 to identify a current user motion state.

In one embodiment, the motion state identification engine 280 determines the probability that a user is in a particular motion state. For example, the motion state identification engine 280 may determine that there is a 95% confidence that the user is running. At the same time, the motion state identification engine 280 may also determine that there is a 25% confidence that the user is bicycling. In one embodiment, this indicates that 19 out of 20 indicators suggest that the user's motion state is running, while 1 out of 4 indicators suggest the user's motion is bicycling. There may be one counter indicator, or one other motion state identification engine 280 that has identified the activity as something other than running.

The confidence/probability that a user is in a particular motion state may be determined based on a number of positive and/or negative events that are satisfied for that user motion state. The confidence/probability may also be determined based on the how close an acceleration measurement is to a threshold of a positive or negative event. For example, if a walking positive event includes an upper acceleration threshold of 3 m/s$^2$, and the positive event was satisfied with a reading of 2.99 m/s$^2$, then a confidence rating may be lower than if the positive event was satisfied with a reading of 2.6 m/s$^2$.

Figure 3A:
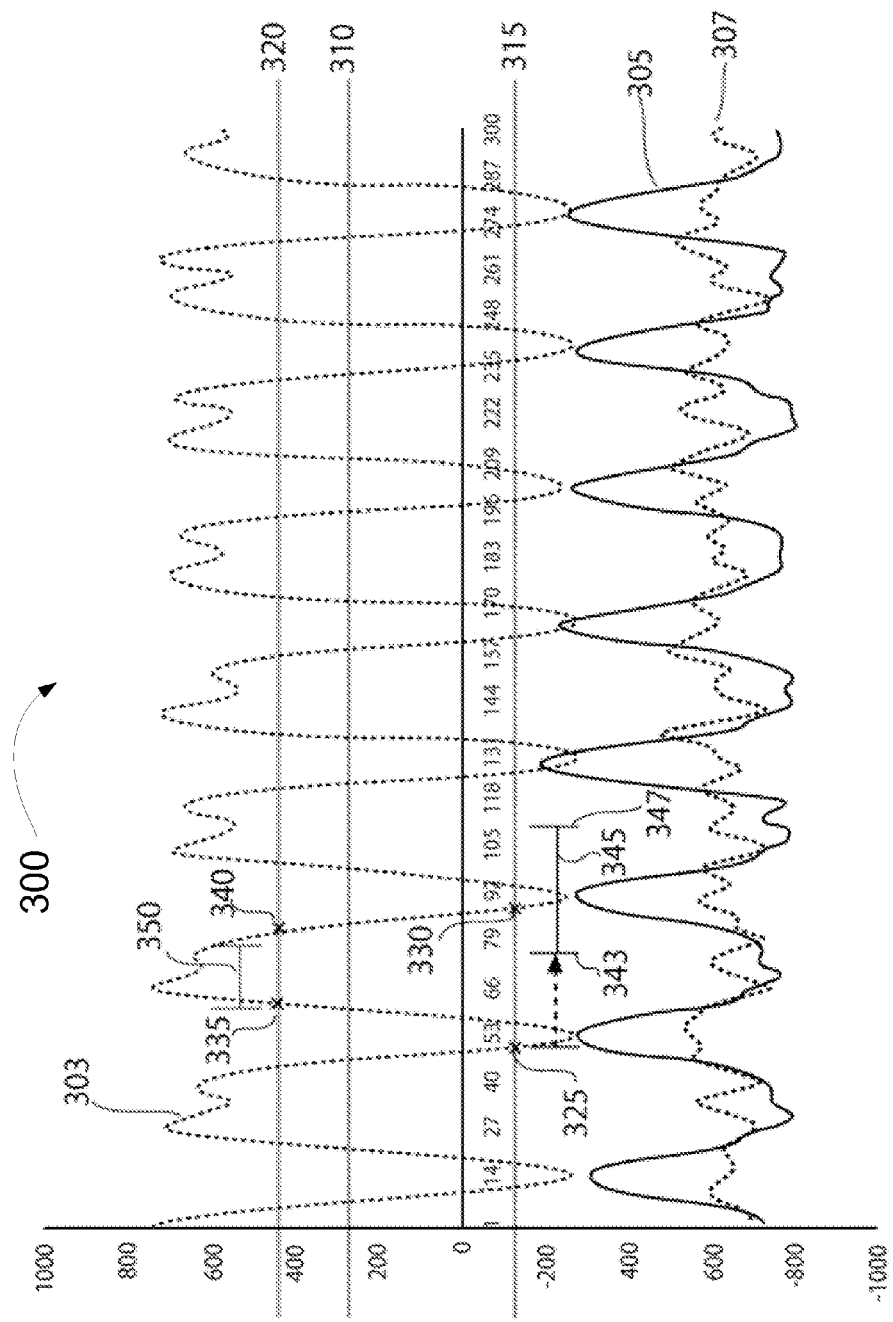
FIG. 3A illustrates a first exemplary motion cycle graph that shows a user engaged in a first user activity.
Figure 3B:
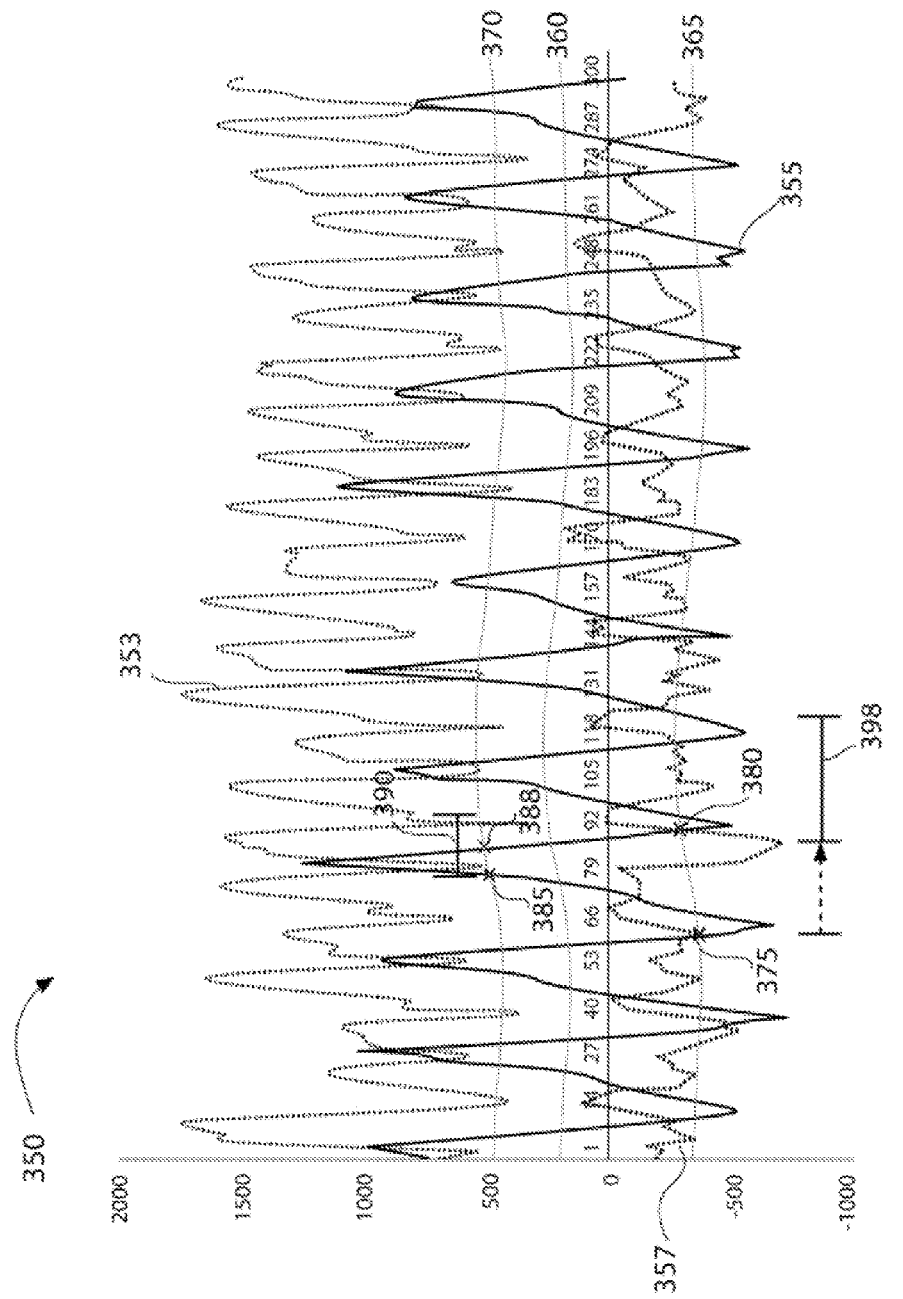
FIG. 3B illustrates a second exemplary motion cycle graph 350 that shows a user engaged in a second user activity.

FIGS. 3A and 3B illustrate examples of motion data which may be used by a motion state identification logic that identifies bicycling by monitoring for positive and negative motion events associated with bicycling, in accordance with embodiments of the present invention. FIG. 3A illustrates a first exemplary motion cycle graph 300 that shows a user engaged in a first user activity as analyzed by a motion state identification logic that identifies bicycling, in accordance with one embodiment of the present invention. The exemplary motion-cycle graph 300 shows acceleration data taken with a single tri-axis inertial sensor. The acceleration at a given period of time is represented for a first axis 303, a second axis 305, and a third axis 307.

The motion state identification engine associated with identifying bicycling, which can be referred to as the bicycling identification logic, monitors for positive events and negative events that occur when certain motion criteria are satisfied. In one embodiment, the bicycling identification logic uses a dominant axis that is defined by measuring the axis with the largest peak to peak difference. This is because in bicycling the user's leg moves in a circle around the axis of the pedal with the downward motion displaying a largest peak to peak difference. In the illustrated figure, the first axis 303 is the dominant axis, because it has the greatest peak to peak difference. In one embodiment, the bicycling identification logic only examines acceleration data along the dominant axis.

In one embodiment, the bicycling identification logic uses a rolling average of accelerations 310 for the dominant axis to set a first threshold 315 and a second threshold 320. The first threshold 315 and second threshold 320 may be set based on offsets from the rolling average of accelerations 310. Alternatively, the first threshold 315 and second threshold 320 may be set based on a percentage of the peak to peak difference, on a percentage of the average of the peak to peak difference, on a percentage of half of the peak to peak difference, or on other criteria. For example, the first threshold 315 may be set at 25% of the peak to peak difference, and the second threshold 320 may be set at 75% of the peak to peak difference.

A first periodic human motion may be detected when the first threshold 315 is first crossed 325 (moving away from zero). This may trigger a positive bicycling event. A second periodic human motion may be detected when the first threshold 315 is crossed a second time 330 (moving away from zero). In one embodiment, if the first threshold 315 is crossed a second time 330 while within a cadence window 345, a positive bicycling event may be triggered. If the first threshold 315 is not crossed 330 while within the cadence window 345, a negative bicycling event may be triggered. The cadence window 345 has a cadence window minimum 343 that opens the cadence window 345 some period of time after the first threshold 315 is first crossed 325, and a cadence window maximum 347 that closes the cadence window 345 some period of time thereafter. In the illustrated example, the first threshold 315 is crossed within the cadence window 345, triggering a positive bicycling event.

The second threshold 320 may be used by the bicycling identification logic to determine a peak shape for the acceleration measurements along the first axis 303. In one embodiment, the bicycling identification logic notes each time the second threshold 320 is crossed. In one embodiment, if the time between when the second threshold 320 is first crossed 335 and second crossed 340 is less than a peak window 350, then a negative bicycling event may be triggered. In one embodiment, unless the time between when the second threshold 320 is first crossed 335 and crossed the second time 340 is greater than or equal to the peak window 350, then a negative bicycling event is triggered. In one embodiment, if the second threshold 320 is crossed within 25-35% or 65-75% of the average of the motion cycle's period, the peak is too steep, and a negative event is triggered. In one embodiment, if the second threshold 320 is crossed within certain percentages of the average of the motion cycle's cadence, a negative event is triggered. In the illustrated example, no negative bicycling events are triggered. Moreover, the illustrated example shows an embodiment in which a sufficient number of positive events are triggered to identify the current user activity as bicycling.

FIG. 3B illustrates a second exemplary motion cycle graph 350 that shows a user engaged in a second user activity as analyzed by a motion state identification logic that identifies bicycling, in accordance with one embodiment of the present invention. The exemplary motion-cycle graph 350 shows acceleration data taken with a single tri-axis inertial sensor. The acceleration at a given period of time is represented for a first axis 353, a second axis 355, and a third axis 357.

The bicycling identification logic monitors for positive events and negative events that occur when certain motion criteria are satisfied. In one embodiment, the bicycling identification logic uses a dominant axis that is defined by measuring the axis with the largest peak to peak difference. In the illustrated figure, the second axis 355 is the dominant axis, because it has the greatest peak to peak difference.

In one embodiment, the bicycling identification logic uses a rolling average of accelerations 360 for the dominant axis to set a first threshold 365 and a second threshold 370. A first periodic human motion may be detected when the first threshold 365 is first crossed 375 (moving away from zero). This may trigger a positive bicycling event. A second periodic human motion may be detected when the first threshold 365 is crossed a second time 380 (moving away from zero). In one embodiment, if the first threshold 320 is crossed a second time 380 while within a cadence window 398, a positive bicycling event may be triggered. If the first threshold 365 is not crossed 380 while within the cadence window 398, a negative bicycling event may be triggered. In the illustrated example, the first threshold 365 is crossed within the cadence window 398, triggering a positive bicycling event.

The second threshold 370 may be used by the bicycling identification logic to determine a peak shape for the acceleration measurements along the second axis 355. In one embodiment, the bicycling identification logic notes each time the second threshold 370 is crossed. The time between when the second threshold 370 is first crossed 385 and second crossed 388 is less than a peak window 390, triggering a negative bicycling event. The negative bicycling event may reset a counter that counts a number of positive bicycling events. Each illustrated peak would trigger a negative bicycling event. Therefore, not enough positive bicycling events are triggered to identify the current user activity as bicycling. FIGS. 3A and 3B illustrate the analysis performed by the bicycle identification logic. Similar analysis is performed for other types of motions.

Returning to FIG. 2, the motion processor 230 may receive positive and negative events from the motion state identification logics 285 of the motion state identification engine 280. The motion processor 230 may also receive dominant axis data from the dominant axis logic 227, rolling average data from the rolling average logic 235, a cadence and period for a current motion cycle from the cadence logic 232, cadence windows from the cadence logic 232, and filtered acceleration data from the filter 220. The motion processor 230 may include a counting logic 260, mode logic 255, and one or more count buffers 265.

In one embodiment, the mode logic 255 receives positive and negative events from the motion state identification logics 285. The mode logic 255 may then determine an appropriate mode for the counting logic 260 based on the received events. The mode logic 255 may also use count buffers 265 in making this determination. Count buffers track periodic human motions, to ensure that the count is maintained while the motion state is correctly identified. In one embodiment, each motion state which is potentially being identified has a separate count buffer. In one embodiment, while in an entry mode, the first count buffer to reach a predetermined value determines which active mode to initiate. In one embodiment, the mode logic 255 includes a plurality of active modes, each active mode corresponding to a different activity. In one embodiment, the mode logic 255 includes an entry mode, an exit mode and a sleep mode. Operating modes are discussed in greater detail below in reference to FIG. 5.

The counting logic 260 may receive data from the dominant axis logic 227, rolling average logic 235, cadence logic 232, and filter 220. The counting logic 260 may use this data to count periodic human motions. In one embodiment, the behavior of the counting logic 260 is determined by its current operating mode.

The counting logic 260 may determine which measurements to use to determine if a periodic human motion has occurred. In one embodiment, the counting logic 260 may monitor accelerations relative to the dominant axis, and select only those measurements with specific relations to the dominant axis for measurement. For example, only accelerations that are along the dominant axis may be selected (e.g., in walking active mode), or alternatively, only accelerations that are approximately perpendicular to the dominant axis may be selected (e.g., in rowing active mode). In one embodiment, the counting logic 260 uses only measurements of acceleration data along the dominant axis. In alternative embodiments, measurements of acceleration data along other axes may also be used.

Selected measurements may be compared to motion criteria to determine whether a periodic human motion has occurred, and to determine what type of periodic human motion has occurred. Examples of motion criteria include comparisons of current measurements to previous measurements, comparisons of current measurements to threshold values, slope analysis, curve fitting analysis, peak analysis, etc. In one embodiment, the same criteria that are used to identify events by the activity identification logics are also used to count periodic human motions. Alternatively, different criteria may be used. In one embodiment, crossing threshold(s) in a motion is used to count. In one embodiment, the motion criteria used are dependent on a current operating mode of the counting logic 260.

The count buffers 265 keep track of a probable count of periodic human motions. In one embodiment, the motion processor 230 includes a plurality of count buffers 265, each associated with a different user activity. Alternatively, a single count buffer may be used to buffer periodic human motions for two or more user activities. In one embodiment, a single count buffer 265 maintains buffers for all user activities.

The behavior of the count buffers 265 may depend on the operating mode of the counting logic 260. For example, in entry mode, a separate count buffer may be maintained for each possible user activity. When the system identifies a periodic human motion that meets the criteria of a particular user activity, the count buffer corresponding to that user activity may be incremented. A detected periodic human motion may meet the criteria for a number of different user activities. Until a current user activity is identified, in one embodiment such motion would be counted by each of the corresponding count buffers 265.

Depending on the current mode, when one of the count buffers 265 reaches a certain number, the motion log 275 may be updated the count from the count buffer. This may also cause the motion logic 255 to place the counting logic 260 in an active mode, for the user motion state associated with the count buffer. In one embodiment, all count buffers 265 are then reset. Thus, the "false motions" counted by the other count buffers 265 are discarded. The number of periodic human motions that are counted by the count buffer before they are moved to the motion log 275 may vary from two to ten or more, depending on the current operating mode. Moreover, in one embodiment count buffers corresponding to different user activities may have different count requirements.

The motion log 275 keeps track of the total number of periodic human motions that have occurred, and the associated activities. In one embodiment, this data is transmitted to a server or remote database. The output of the motion log 275, in one embodiment, is made available to the user. In one embodiment, the user can view the various activities, and associated data through a web page. In one embodiment, the user can see an overall activity level on a per hour, per day, per week, or other basis, in addition to being able to see the individual activities comprising the overall activity level.

In one embodiment, one or more programs 290 are coupled to the motion state identification system 200. The one or more programs 290 may receive an identification of a current user motion state from the motion state identification system 200. In one embodiment, the programs 290 receive motion state identification information from the motion state identification engine 280. In another embodiment, the programs 290 receive motion state identification information from the motion processor 230. In one embodiment, the identification of the current user motion state is received along with a confidence rating for the current user motion state. For example, a program may receive information indicating that there is a 98% chance that the user is walking. In another embodiment, the identification of multiple possible current user motion states is received along with confidence ratings for each possible user motion state. For example, a program may receive an indication that there is a 70% confidence that the user is running and a 30% confidence that the user is bicycling.

In one embodiment, the programs 290 receive additional information from the motion identification system 200. The additional information may be information that is derived from the acceleration measurements (hereinafter referred to as motion related information). For example, the programs 290 may receive information on a user's current cadence, a user's current rolling average, a current dominant axis, counted periodic human motions, etc.

In one embodiment, the programs 290 poll the motion identification system 200 to determine a current user motion state and/or additional user motion related information. The programs 290 may poll the motion identification system 200 continuously, periodically, or upon occurrence of predefined events (e.g., when a music player application begins to play a new song). Alternatively, current motion related information may be posted to a current motion related information cache (not shown). In one embodiment, the motion related information cache may be maintained with current up-to-date information by motion identification system 200. Programs 290 may then obtain data from the cache to determine a current user motion state, including current cadence, current dominant axis, etc.

In one embodiment, the programs subscribe to one or more motion related information services through subscription logic 292. Each subscription entry may identify what types of motion related information that the subscription logic 292 of motion identification system 200 is to send to the programs 290. Each subscription entry may also identify when to send updated motion related information to the programs 290. For example, a subscription may cause the motion state identification system 200 to send cadence updates every 10 seconds and user activity updates every 5 seconds. Alternatively, a subscription may cause the subscription system 292 to send a current user activity update whenever a current user motion state changes.

In one embodiment, a program 290 uses the received user motion state information to adjust settings of the program 290. For example, if the program 290 is a music player application, it may adjust a volume level and/or the music tempo based on the detected user motion state. If, for example, a user is detected to be running, the volume and/or music tempo may be increased. In another example, if the program is a telephony application, the ringer and/or speaking volume may be increased or decreased based on the detected user motion state. Other settings, such as what user gestures are used as commands may also be adjusted based on the detected user motion state.

In another embodiment, the program uses the received motion state information to adjust settings of the program 290. For example, a music player application may adjust a music tempo to match a detected user cadence. In another example, the music application may generate a playlist of songs that match a user's current cadence. This makes it easier for the user to maintain a cadence by matching the music tempo. Moreover, the music application may be integrated with a user fitness application that indicates for the user to speed up or slow down by selecting songs that are faster or slower in tempo than the user's current cadence.

Figure 4A:
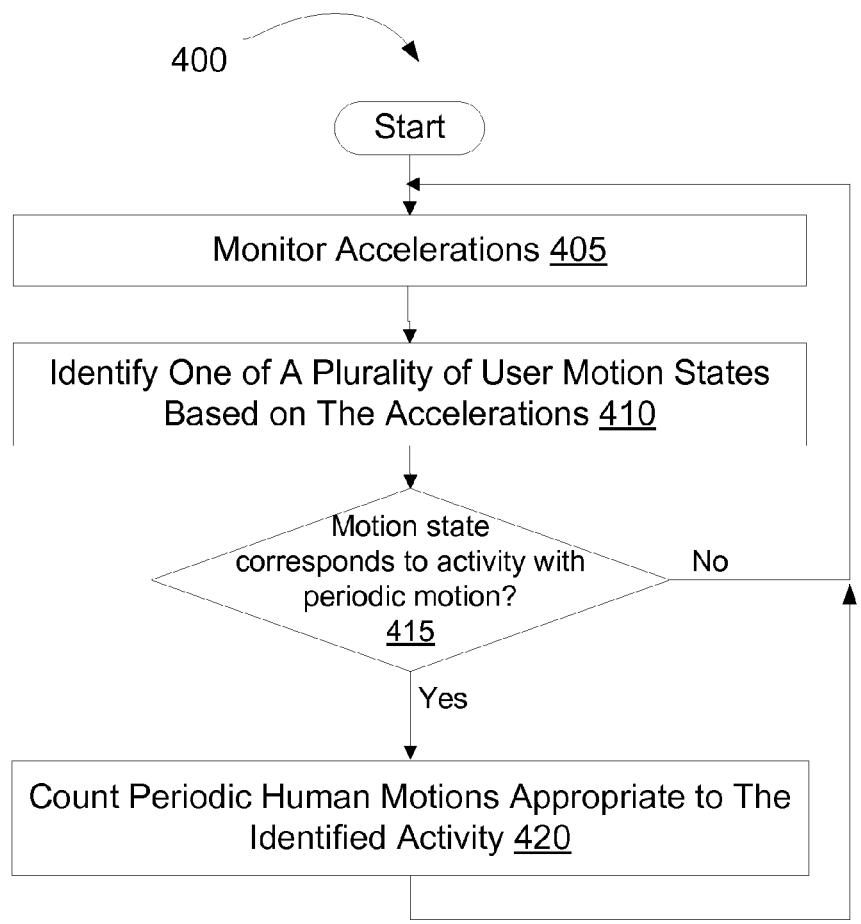
FIG. 4A illustrates a flow diagram for a method of monitoring user motion state with an inertial sensor, in accordance with one embodiment of the present invention.

FIG. 4A illustrates a flow diagram for a method 400 of determining a motion state, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 400 is performed by the electronic device 100 of FIG. 1. In one embodiment, method 400 is performed by the motion identification system 200 of FIG. 2.

Referring to FIG. 4A, method 400 begins with monitoring accelerations (block 405). Accelerations may be monitored with an inertial sensor, or other acceleration monitoring device. The monitored acceleration may include filtered and processed acceleration data, as described above. At block 410, the motion is identified as corresponding to one of a plurality of motion states based on the accelerations. The motion states may include user activities involving periodic human motions, or other motion states which do not require a user to be performing periodic human motions. At block 415, the process determines whether the motion state corresponds to an activity that includes periodic human motions. If so, at block 420, periodic human motions are counted appropriate to the identified activity. Examples of identifiable user activities include, walking, running, inline skating, rowing, exercising on an elliptical machine, and bicycling. Other user activities may also be identified. The process then returns to block 410, to continue monitoring accelerations. If the motion state does not correspond to an activity with periodic motions, the process returns to block 410, to continue monitoring accelerations.

Periodic human motions corresponding to multiple different predetermined user activities may be identified in embodiments of the present invention. Moreover, in one embodiment, new user activities may be added to the list of recognized periodic human motions. To add such periodic human motions to the predetermined user activities, a user may record a new user activity.

Figure 4B:
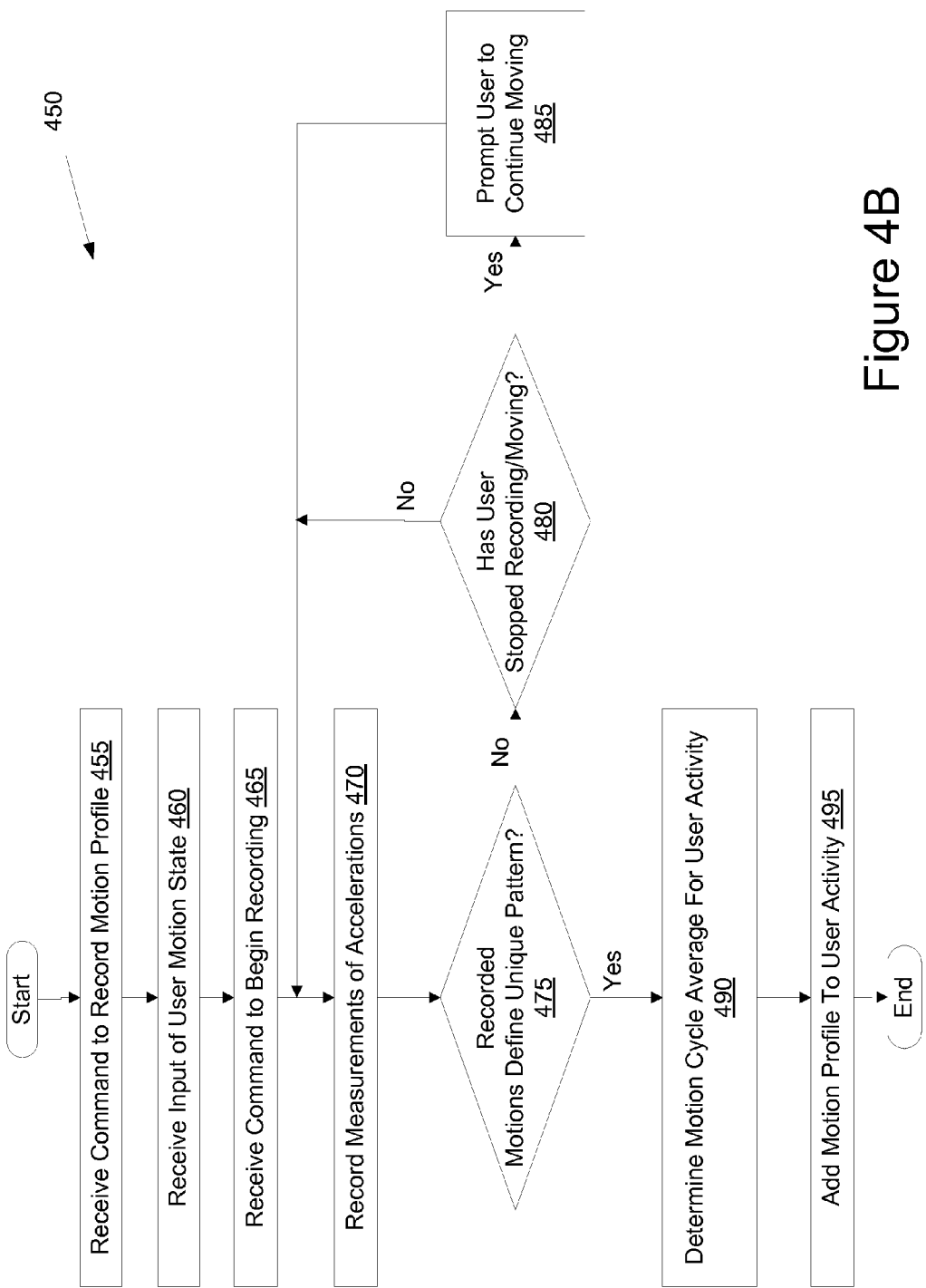
FIG. 4B illustrates a flow diagram for a method of recording a motion state, in accordance with one embodiment of the present invention.

FIG. 4B illustrates a flow diagram for a method 450 of recording a motion profile, in accordance with one embodiment of the present invention. Method 450 may be used to record new user motion states or activities, or to calibrate existing activities to a particular user. Calibration of existing user activities may improve counting accuracy. Calibration may be useful when the user's activity is performed in an unusual way. For example, if the user is riding a recumbent bicycle, the motions will not match the traditional "bicycling" motion cycle graph. The method 450 may be performed by processing logic that may comprise hardware (e.g., circuitry, dedicated logic, programmable logic, microcode, etc.), software (such as instructions run on a processing device), or a combination thereof. Method 450 may be performed by the electronic device 100 of FIG. 1, and by the motion identification system 200 of FIG. 2.

Referring to FIG. 4B, the method 450 begins by receiving a command to record a motion profile (block 455). At block 460, input is received that indicates the user activity for which the motion profile will be recorded. In one embodiment, the system may enable the user to select one of a displayed list of existing user activities. In one embodiment, the user may select one of the displayed user activities or may choose to identify a new user activity to be associated with the motion profile. If a motion profile is to be recorded for a new user activity, the user may be prompted to enter a name for the new user activity.

At block 465, a command is received to begin recording. At block 470, measurements of accelerations are recorded. The measurements of accelerations are recorded while a user performs the user activity for which a motion profile is to be recorded.

At block 475, the process determines whether the recorded measurements define a unique pattern. In one embodiment, measurements of accelerations are recorded until a unique pattern can be determined. A unique pattern differentiates the recorded pattern from other motion profiles.

If a unique pattern has not yet been identified, the process determines if the user has stopped the recording and/or motion, at block 480. In one embodiment, if the user stops recording before such a unique pattern is identified, the system prompts the user to continue recording, at block 485. The process then returns to block 470 to continue recording motion data. If the user has not stopped the recording, the process continues directly to block 470. The time to determine a pattern may range from recording a single motion cycle, to recording many motion cycles, which may occur over a single second to minutes or even longer. In one embodiment, user input may be received to specify the period of a current motion cycle. For example, a user may push a button, make a certain movement, make a loud noise, etc. each time a new periodic human motion ends (e.g., each time a step is completed). This may reduce the number of motion cycles that need to be recorded in order to determine a pattern from the recorded measurements. Alternatively, the period of the motion cycle is determined without user input. In one embodiment, the system utilizes at least two full motion cycles to identify the pattern. Without any user input as to the period or motion type, it is likely that more than two motion cycles would be needed to identify the pattern.

If at block 475, a unique pattern has been identified, the process continues to block 490. In one embodiment, the user is notified that the new activity pattern has been successfully identified. At block 490, in on embodiment a motion cycle average may be determined for the activity. Once a unique pattern of accelerations is determined for the activity, at block 495, the motion profile may be added to either an existing user activity or to a new user activity.

The unique pattern of accelerations may also be used to determine (set) positive and/or negative events for the activity. For example, if the unique pattern of accelerations shows a repeated sharp acceleration peak along a dominant axis, a sharp acceleration peak along the dominant axis may be added as a new positive event and/or a gradual peak along the dominant axis may be added as a new negative event. If method 450 was initiated to calibrate an existing user profile, the calibration may include adding new positive and/or negative events to the existing positive and/or negative events. If method 450 was initiated to record a new activity, new positive and/or negative events may be assigned to facilitate future identification of the new activity. It is possible that the motion recording does not define a unique pattern even after a considerable time. In one embodiment, after a period the system may indicate to the user that the motion cycle matches an existing activity. The user may concur that the existing activity does match the attempted new motion cycle pattern. In that case, the motion cycle pattern may be used to adjust the motion cycle associated with the identified activity. Alternatively, in one embodiment the recording process may fail.

Figure 5:
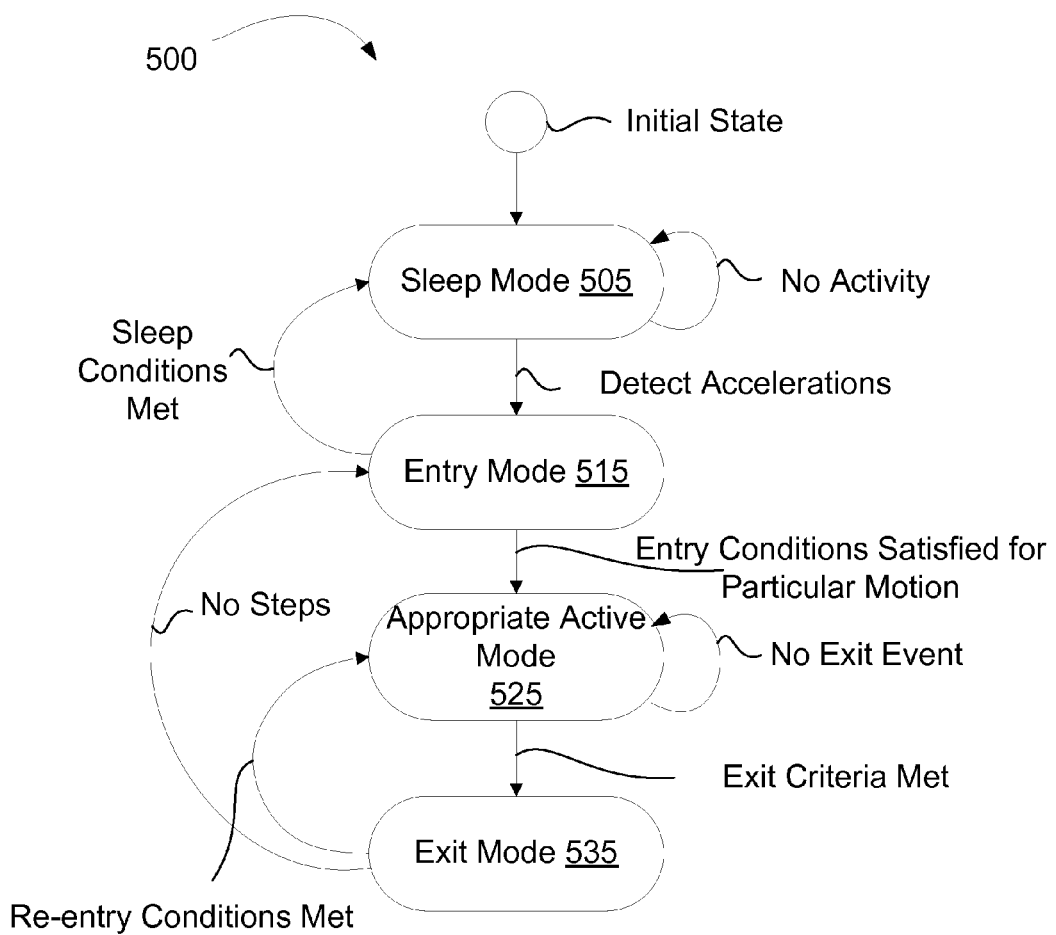
FIG. 5 shows a state diagram for the behavior of a system for monitoring user motion state, in accordance with one embodiment of the present invention.

FIG. 5 shows a state diagram for the behavior 500 of a system for monitoring user motion states, in accordance with one embodiment of the present invention. The system may have multiple operating modes (states) that are navigated between by processing logic that may comprise hardware (e.g., circuitry, dedicated logic, programmable logic, microcode, etc.), software (such as instructions run on a processing device), or a combination thereof. In one embodiment, behavior 500 is the behavior of the electronic device 100 or a subset of the device shown in FIG. 1. In one embodiment, behavior 500 is the behavior of the electronic device or inertial sensor (s) within motion identification system 200 of FIG. 2.

The behavior 500 may include multiple operating modes for monitoring human activity: a sleep mode, an entry mode, one or more active modes, and an exit mode. In alternative embodiments, more or fewer modes may be used. In one embodiment, only two modes are used: active mode and non-active mode. The active mode is entered once periodic human motions are detected, while the non-active mode is used for all other states. In alternative embodiments, multiple inactive modes and/or active modes are used. To navigate between modes, certain conditions must be met. The conditions may include exit conditions for terminating an active mode and entry conditions for initiating inactive modes. Each mode has one or more exit and entry conditions.

Use of different conditions for different operating modes increases the reliability of the device that is monitoring the human activity. For example, once an object (e.g., a person) is moving, they are more likely to remain moving than to stop. Likewise, if a person is not moving, they are more likely not to move than to begin moving. Moreover, if a person is running, he is more likely to continue running than to begin bicycling. These principles can be applied by requiring more stringent conditions to be met for a device to initiate an active mode than to continue the active mode. The different modes may each have rules that reflect what is more likely to happen for subsequent measurements. This may reduce or eliminate the number of uncounted periodic human motions and/or false periodic human motion counts.

Referring to FIG. 5, operating modes in one embodiment include a sleep mode 505, an entry mode 515, an active mode 525, and an exit mode 535. In one embodiment, the power level of the system or device is linked to these modes.

The first mode is the sleep mode 505. When no activity (acceleration) is detected, the system remains in sleep mode 505. When acceleration is detected, an entry mode 515 is initiated. In one embodiment, in sleep mode 505 the inertial sensor has a slow sample rate, thereby reducing power consumption of the system. In one embodiment, in sleep mode 505 only those portions of the processor needed to monitor the accelerometer are awake, and the remaining parts of the processor are placed in a sleep mode.

Once in entry mode 515, in one embodiment the sampling rate of the inertial sensor is increased to ensure that acceleration is monitored to detect periodic human motions. In entry mode 515, periodic human motions appropriate to all identifiable user activities may be monitored. Therefore, in one embodiment, the sampling rate is sufficiently high to properly detect the fastest possible activity. In another embodiment, the sampling rate is adjusted based on the actual observed motion level. For example, when the user is strolling, the sampling rate need not be as fast as when the user is utilizing gesture commands or riding a bicycle.

When entry conditions are satisfied for a particular user activity, an appropriate active mode 525 is initiated. The sampling rate is then adjusted to be appropriate for the activity being detected, in one embodiment. In one embodiment, if no entry conditions for any of the identifiable user activities are detected in a period of time, sleep mode 505 is reinitiated. In another embodiment, sleep mode 505 is only initiated if no motion is detected.

Once in the appropriate active mode 525, acceleration data is monitored to count periodic human motions according to a predefined set of rules or motion criteria as discussed above. According to one of these criteria, periodic human motions are expected to occur within a set interval (e.g., within a cadence window). When a periodic human motion is counted within the set interval, then the current active mode 525 is continued. When a periodic human motion is not detected within the set interval, an expected periodic human motion has not occurred, and an exit mode 535 is initiated.

In exit mode 535, processing logic determines whether re-entry conditions are met. Reentry conditions are met when subsequent periodic human motions consistent with the last active mode are observed. By using an exit mode to verify that the activity has ceased, the system reduces the chances that a single stumble by the user triggers a full re-analysis of the motion. When the re-entry conditions are met, the appropriate active mode 525 is reinitiated. If the re-entry conditions are not met within a certain time frame, the process initiates entry mode 515 again. From entry mode 515, any appropriate active mode 525 may again be entered into if certain entry conditions are satisfied, or the process may return to sleep mode 505.

Figure 6:
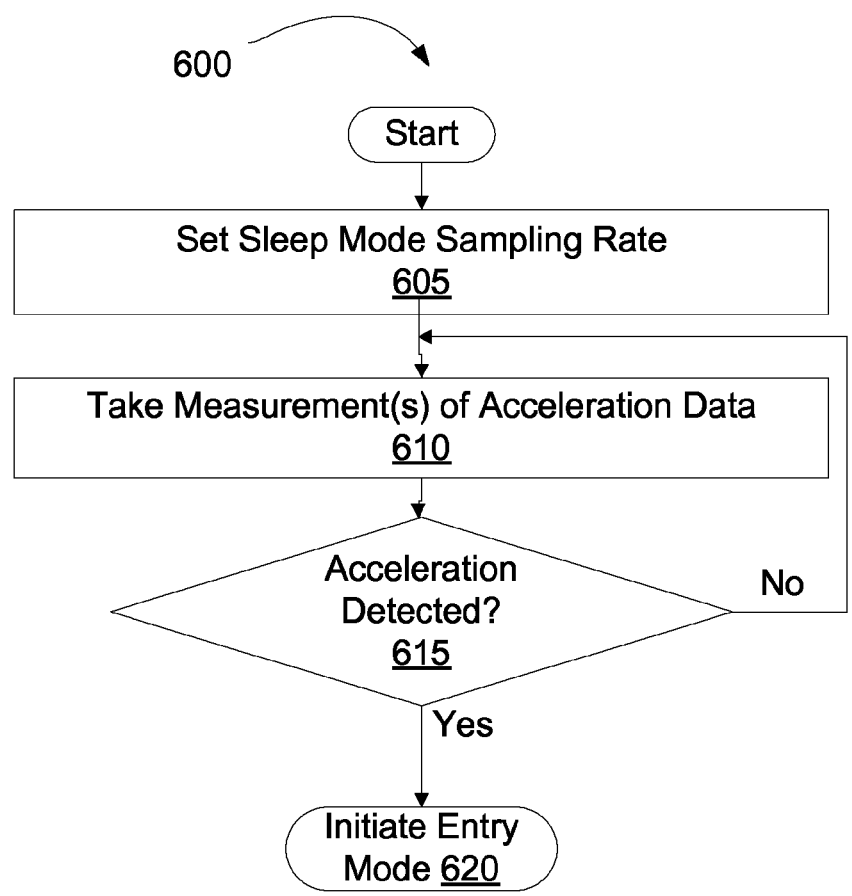
FIG. 6 illustrates a flow diagram for a method of operating an electronic device in sleep mode, in accordance with one embodiment of the present invention.

FIG. 6 illustrates a flow diagram for a method 600 of operating an electronic device in sleep mode, in accordance with one embodiment of the present invention. In one embodiment, method 600 corresponds to the sleep mode 505 of FIG. 5. In one embodiment, the method 600 may begin when no relevant acceleration has been detected for a predetermined time interval, or when no periodic human motions have been detected for a predetermined time interval. In one embodiment, when no acceleration above a threshold value is detected for a set period of time, the sleep function is initiated. In another embodiment, when only motion signatures indicative of an activity that does not need to be monitored is detected, the sleep function is initiated. For example, when the motion signature of driving is detected, the sleep function may be initiated. The time period that elapses before the sleep mode is initiated may be fixed, or it may be adjusted automatically by processing logic or based on user input (e.g. in response to a user selection of desired battery longevity versus desired performance, or based on the last measured cadence window).

Referring to FIG. 6, method 600 begins with setting a sleep mode sampling rate (block 605). In one embodiment, a low sampling rate is set. This reduces power consumption and prolongs battery life. In one embodiment, the sleep mode sampling rate is a fixed value. In alternative embodiments, the sleep mode sampling rate can be modified automatically by processing logic based on certain criteria such as time of day, user behavior patterns, etc., or based on user input.

In one embodiment, a sampling function is periodically executed in sleep mode, wherein the sampling function samples acceleration data at a set sampling rate for a set time period. For example, the sampling function may be executed every ten seconds for the duration of one second, and a sampling rate of fifty measurements per second may be set for that one second of operation. In one embodiment, the sampling function repeats at a relatively slow rate (e.g., once every 10 seconds), and the sampling rate within the sampling function is relatively high (e.g., 50 Hz). The sampling function may be used to detect unwanted motion signatures, or to maintain a device in low power sleep mode, for example, while a user is driving in a car.

In one embodiment, the sleep mode sampling rate is set to zero. The sleep mode sampling rate may be set to zero, for example, when an inertial sensor has 'inertial wakeup' functionality. Inertial wakeup functionality enables processing logic to switch from sleep mode to entry mode when an acceleration exceeding a set threshold is detected. The inertial wakeup may be used to simultaneously exit sleep mode and power-up additional functionality.

At block 610, measurements of acceleration data are taken. At block 615, processing logic determines whether or not relevant acceleration is detected. Relevant acceleration includes acceleration that meets certain criteria. In one embodiment, the criteria include a lower threshold and an upper threshold. In alternative embodiments, other criteria may also be used, such as a requirement that acceleration be continuously measured for a preset time period.

When no relevant acceleration is detected, or when the 'inertial wakeup' pin has not triggered (for inertial sensors having 'inertial wakeup functionality'), sleep mode continues, and further measurements of acceleration data are taken at the set sleep mode sampling rate (block 610). When acceleration is detected, sleep mode is terminated and entry mode is initiated (block 620). In one embodiment, the acceleration that is detected and its rate of change must meet certain criteria to terminate sleep mode.

Figure 7A:
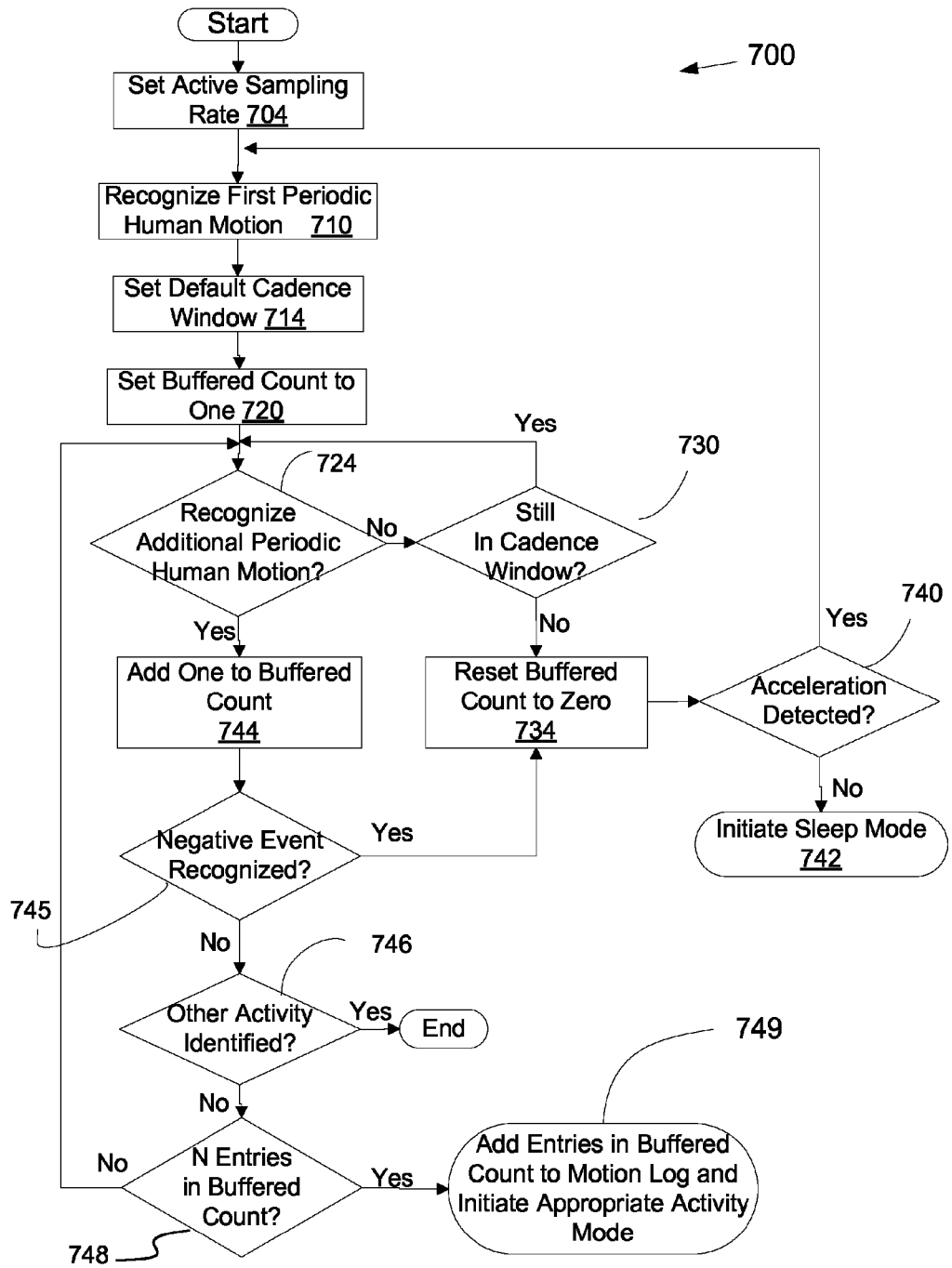
FIG. 7A illustrates a flow diagram for a method of operating an electronic device in entry mode, in accordance with one embodiment of the present invention.

FIG. 7A illustrates a flow diagram for a method 700 of operating an electronic device in entry mode, in accordance with one embodiment of the present invention. In one embodiment, method 700 corresponds to the entry mode 515 of FIG. 5. The entry mode may be initiated when a user first begins an activity in which periodic human motions may be detected. In one embodiment, the method 700 begins when any relevant acceleration is detected. In one embodiment, entry mode is initiated when a measurement of acceleration that meets certain criteria has been detected. In one embodiment, method 700 is initiated when a sleep mode is terminated. In one embodiment, method 700 is performed concurrently by each of the activity identification logics 285 of FIG. 2 when the motion identification system 200 and/or the counting logic 260 of the electronic device are in entry mode.

Referring to FIG. 7A, method 700 begins by setting the sampling rate to an active sampling rate (block 704). The active sampling rate is set to facilitate accurate measurements of motion states, and periodic human motions, and may be a fixed or a dynamically variable rate. A variable sampling rate may automatically adjust depending on detected motion frequency/level, a period of a detected motion cycle's cadence, may be user adjusted, may adjust based on applications being run by processing logic, or other aspects of the motion data or device state. The active sampling rate may be set to anywhere between about 10 and about 200 Hz in one embodiment. In one embodiment, the active sampling rate is set to about 15 to 40 Hz.

At block 710, a first periodic human motion is recognized. A periodic human motion, in one embodiment, is a motion cycle which includes at least two recognized states, at least one of which recurs. For example, the motion cycle may be motion A, B, C, repeating. A periodic human motion is recognized, in one embodiment, when motions A, B, C, A (or B, C, A, B) are identified. Since no previous periodic human motions have been measured, and there is no cadence window, the first periodic human motion may be recognized at any time. Once a first periodic human motion is recognized, a default cadence window is set (block 714). The default cadence window may have a minimum and maximum such that periodic human motions will be counted for most or all possible motion cycle cadences. A different default cadence window may be set for each activity. In one embodiment, a separate instance of method 700 is run for each instance of activity identification logic.

In one embodiment, an initial default value for the cadence window is set wide enough to accommodate all users. In one embodiment, the default cadence window is then dynamically adjusted to match the specific user. Processing logic may 'learn' (adapt to) a particular user, and may become more accurate as periodic human motions are counted. Processing logic that has the ability to learn or adapt to different users may create an individualized profile for each user. Multiple profiles may also be created for each user, the different profiles reflecting different user activities. For example, a first profile might be created for a user's running and a second profile may be created for a user's walking. Processing logic may switch between different profiles automatically or manually based on user input. In one embodiment, processing logic compares a current cadence and/or motion cycle pattern to stored profiles. When a current cadence or motion cycle pattern matches that of a stored profile, that profile may be activated.

At block 720, a buffered count is set to one. At block 724, processing logic determines whether an additional periodic human motion is recognized. An additional periodic human motion may be recognized if the motion cycle meets all the necessary criteria. Different criteria may be used for each of the different user activities. One embodiment of these criteria is discussed below with reference to FIG. 10.

Returning to FIG. 7A, if an additional periodic human motion is recognized, method 700 continues to block 744. If no additional periodic human motions are recognized, then processing logic determines whether the time is still within the cadence window (block 730). If there is still time within the cadence window, the process returns to block 724 to determine whether an additional periodic human motion is recognized. If the cadence window has closed, then the buffered count is reset to zero (block 734). The process then continues to block 740.

At block 740, processing logic determines whether any relevant acceleration is detected. If no relevant acceleration is detected, then sleep mode is initiated (block 742). If some relevant acceleration is detected, then processing logic returns to block 710 to monitor acceleration data and attempt to identify a periodic human motion.

If at block 724 an additional periodic human motion was recognized, the process continues to block 744. At block 744, an additional periodic human motion is added to the buffered count. Processing logic then checks whether any negative events have been recognized (block 745). A negative event is an indicator that the motion does not belong the activity category being tested. If a negative event is recognized, then the process continues to block 734, and the buffered count is reset to zero. If no negative events are recognized, then the process continues to block 746.

At block 746 the process determines whether another user activity associated with a different instance of method 700 has been identified. That is, it determines whether another activity has been conclusively identified. If another user activity has been identified, then the buffer is emptied and the process ends. If no other user activity has been identified yet, then the process continues to block 748.

At block 748, processing logic checks whether there are N periodic human motions in the buffered count. N may be preset, or may be based on a confidence interval detected. If not, the process returns to block 724 to continue in entry mode. When the number of periodic human motions in the buffered count reaches N, the buffered periodic human motions are added to a motion log, and an appropriate active mode is entered into (block 749). The entry mode then terminates, and all buffers are reset to zero.

Figure 7B:
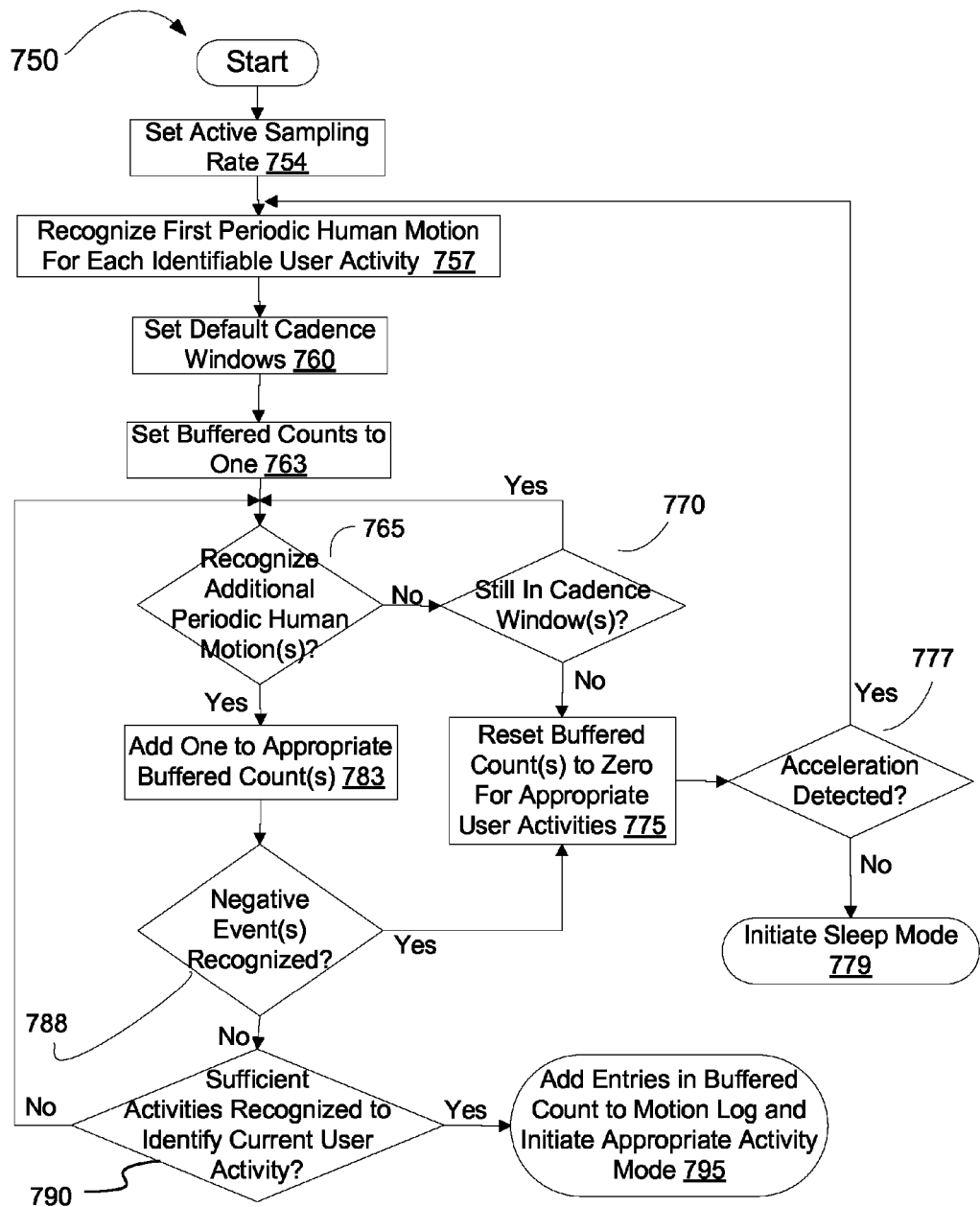
FIG. 7B illustrates a flow diagram for a method of operating an electronic device in entry mode, in accordance with another embodiment of the present invention.

FIG. 7B illustrates a flow diagram for a method 750 of operating an electronic device in entry mode, in accordance with another embodiment of the present invention. In one embodiment, method 750 corresponds to the entry mode 515 of FIG. 5. The entry mode may be initiated when a user first begins an activity in which periodic human motions may be detected. In one embodiment, the method 750 begins when any relevant acceleration is detected. In one embodiment, entry mode is initiated when a measurement of acceleration that meets certain criteria has been detected. In one embodiment, method 750 is initiated when a sleep mode is terminated.

Referring to FIG. 7B, method 750 begins by setting the sampling rate to an active sampling rate (block 754). The sampling rate, in one embodiment, depends on the highest sampling rate required by a potentially recognizable activity.

At block 757, a first periodic human motion is recognized for each identifiable user activity. Since no previous periodic human motions have been measured, and there is no cadence window, the first periodic human motion may be recognized at any time. Once a first periodic human motion is recognized, default cadence windows are set (block 760). Default cadence windows may be set for each type of identifiable user activity.

At block 763, a buffered count is set to one for each of the identifiable user activities. At block 765, processing logic determines whether additional periodic human motions are recognized for each of the identifiable user activities. Different criteria may be used to separately determine whether an additional periodic human motion is recognized for each of the user activities.

For user activities for which an additional periodic human motion is recognized, method 750 continues to block 783. Concurrently, for user activities for which no additional periodic human motion is recognized, the process continues to block 770. At block 770, the process determines whether the time is still within the appropriate cadence window for each appropriate user activity. If there is still time within the appropriate cadence window, the process returns to block 765 for that user activity. If the cadence window has closed, then the appropriate buffered count is reset to zero (block 775). The process then continues to block 777.

At block 777, processing logic determines whether any relevant acceleration is detected. If no relevant acceleration is detected for any of the user activities, then sleep mode is initiated (block 779). If some relevant acceleration is detected for any user activity, then processing logic returns to block 757 to await recognition of another first periodic human motion for the appropriate user activity.

If at block 765 an additional periodic human motion was recognized, the process continues to block 783 for the appropriate user activity, and an appropriate periodic human motion is added to an appropriate buffer count.

At block 788, processing logic checks whether any negative events have been recognized for each appropriate user activity. For user activities for which a negative event is recognized, the process continues to block 775, and the appropriate buffered count is reset to zero. For user activities for which no negative event is recognized, the process continues to block 790.

At block 790 the process determines whether sufficient periodic human motions have been recognized to identify a current user activity. If sufficient periodic human motions have been recognized for a particular user activity, the process continues to block 795. At block 795, the entries in the appropriate buffered count are added to the motion log, and an active mode is initiated for the identified activity.

Figure 8:
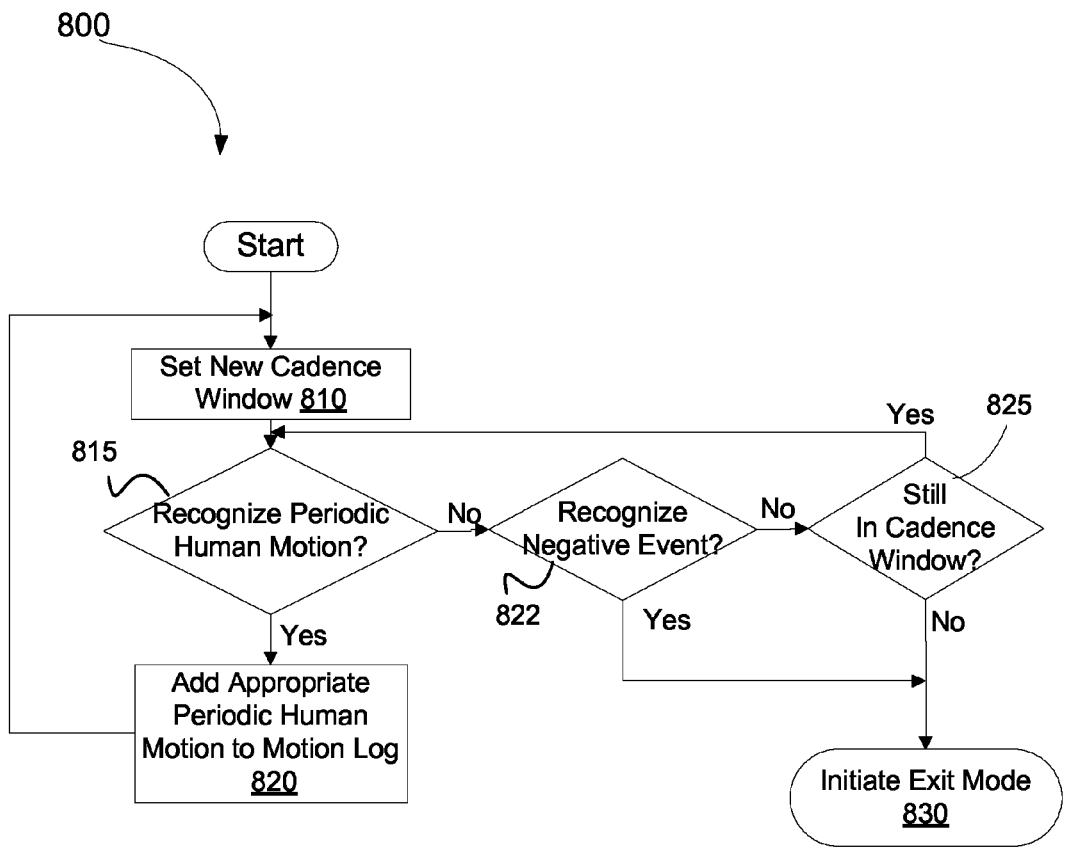
FIG. 8 illustrates a flow diagram for a method of operating an electronic device in an active mode, in accordance with one embodiment of the present invention.

FIG. 8 illustrates a flow diagram for a method 800 of operating an electronic device in an active mode, in accordance with one embodiment of the invention. In one embodiment, method 800 corresponds to the appropriate active mode 525 of FIG. 5. The active mode may be initiated when a particular motion state has been identified. In one embodiment, method 800 is initiated when an entry mode is terminated, and/or when an exit mode is terminated.

Referring to FIG. 8, method 800 begins by setting a cadence window (block 810). The cadence window may be set based on previous measurement data. In one embodiment, the cadence window is set based on a rolling average of motion cycle periods. In one embodiment, the cadence window may be identical to an appropriate cadence window used during entry mode. Once the cadence window is set, measurement data is checked to determine whether an additional periodic human motion is recognized (block 815). If an additional periodic human motion is recognized, then it is added to the motion log (block 820). If no additional periodic human motion is recognized, then the process determines whether a negative event has been recognized 822. If a negative event has been recognized, the process continues to block 830, and exit mode is initiated. If no negative event has been recognized, the process continues to block 825.

At block 825, the process determines whether the current measurement was taken within the cadence window. If the cadence window is still open, the process returns to block 815. If the cadence window has elapsed, then an expected periodic human motion was not identified, and an exit mode is initiated (block 830).

Figure 9:
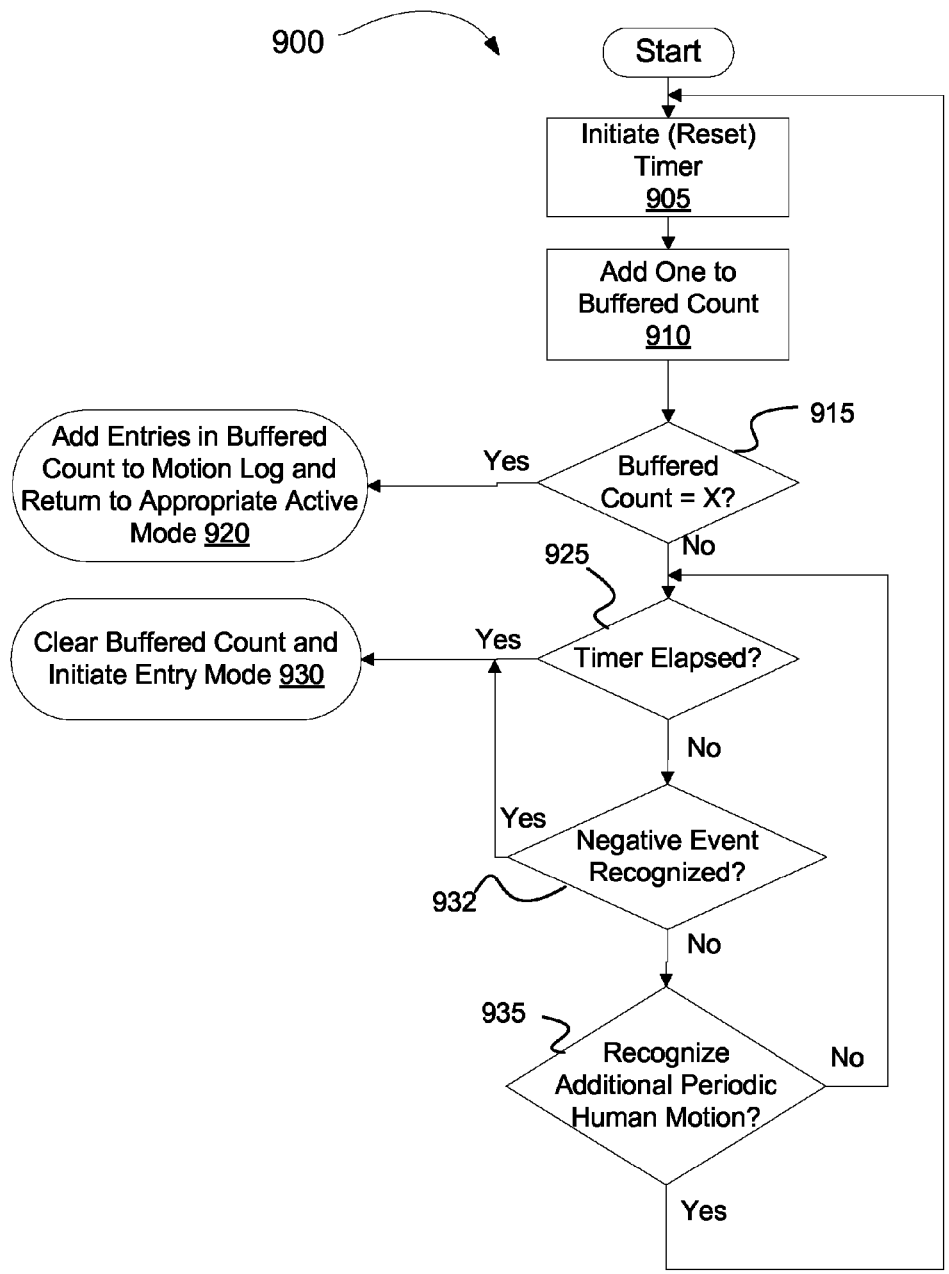
FIG. 9 illustrates a flow diagram for a method of operating an electronic device in an exit mode, in accordance with one embodiment of the present invention.

FIG. 9 illustrates a flow diagram for a method 900 of operating an electronic device in exit mode, in accordance with one embodiment of the present invention. In one embodiment, method 900 corresponds to the exit mode 535 of FIG. 5. The exit mode may be entered into when an expected periodic human motion is not identified in an active mode.

In one embodiment, the requirement(s) for changing from exit mode to an active mode are less strict than the requirement(s) for switching from entry mode to an active mode. Processing logic may assume that when a user has recently performed a periodic human motion, the user is most likely repeat the same periodic human motion. For example, a user who is inline skating is much more likely to continue skating movements than to break into a jog. Furthermore, momentary interruptions of activities occur when people stumble, or miss a step, or otherwise do something unexpected while continuing the underlying activity. Processing logic may also assume that if a user is currently inactive, it is most likely that the user will remain inactive. These assumptions may be implemented by imposing more stringent requirements to switch from entry mode to an active mode than to change from exit mode to an active mode. The requirements to remain in an active mode may be even less stringent than the requirements to initiate the active mode, whether from the entry mode or from the exit mode.

An expected periodic human motion may not be identified, for example, when a user stops moving, when extraneous movements such as gestures are made that interfere with the periodic human motion count, or when a device orientation is changed as a periodic human motion occurs. In one embodiment, the exit mode assumes that a periodic human motion has been missed, so that if the exit mode determines that a user is still continuing the same activity, the originally uncounted periodic human motion is not missed.

The process begins by initiating a timer (block 905). The timer measures the amount of time that has passed since a periodic human motion has been identified. In one embodiment, the timer is a countdown timer that terminates exit mode when the timer reaches zero. In one embodiment, the timer starts counting when a cadence window minimum is reached, and stops counting when a cadence window maximum is reached. In an alternative embodiment, the timer starts counting as soon as the exit mode is initiated, and stops counting when a cadence window maximum is reached.

At block 910, a periodic human motion is added to a buffered count. At block 915, processing logic determines whether the buffered count is equal to X, where X is the number of identified periodic human motions that, when reached, return processing logic to an appropriate active mode. In one embodiment, X is between 3 and 8. In one embodiment, the value of X is dependent upon the specific active mode that exit mode was initiated from. If the buffered count is equal to X, then the buffered periodic human motions are added to motion log and the previous (appropriate) active mode is reinitiated (block 920). If the buffered count is not equal to X, then processing logic proceeds to block 925.

At block 925, processing logic determines whether the timer has timed out (allotted time has elapsed). In one embodiment, the timer times out when no periodic human motions are counted within a cadence window. In one embodiment, the timer times out when no periodic human motions are counted in two or more cadence windows. If the allotted time has elapsed, then the buffered count is cleared, and entry mode is initiated (block 930). If the allotted time has not elapsed, then processing logic determines whether a negative event has occurred (block 932). If a negative event has occurred, the method returns to block 930. If no negative event has occurred, the method proceeds to block 935.

At block 935, processing logic determines whether an additional periodic human motion is recognized. If an additional periodic human motion is recognized, then the timer is reset (block 905), the buffered count is incremented by one (block 910), and on the process continues to block 915. If a periodic human motion is not recognized, then processing logic returns to block 925 to determine whether the timer has elapsed.

Figure 10:
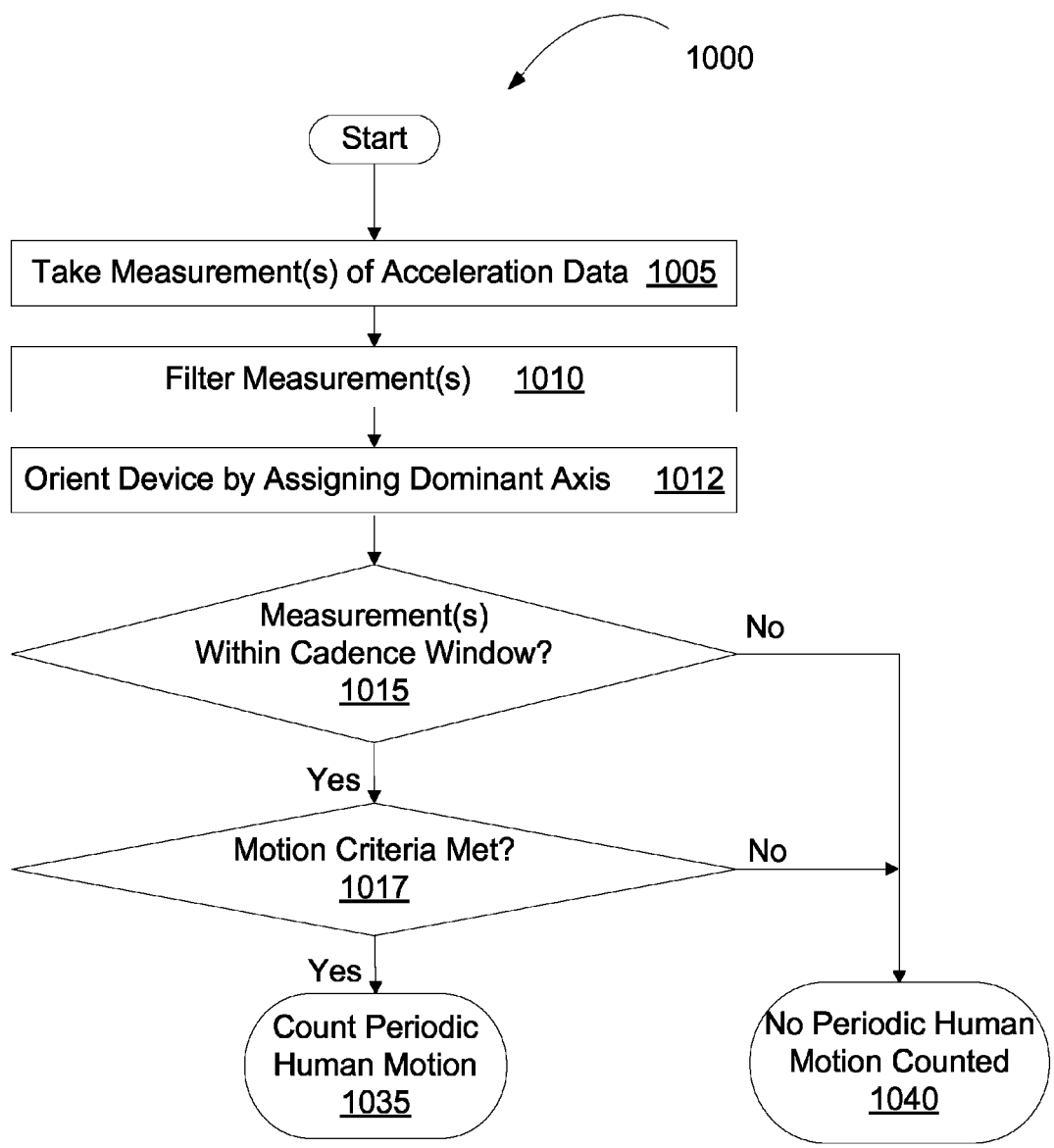
FIG. 10 illustrates a flow diagram for a method of recognizing a user motion state, in accordance with one embodiment of the present invention.

FIG. 10 illustrates a flow diagram for a method 1000 of recognizing a periodic human motion, in accordance with one embodiment of the present invention. In one embodiment, method 1000 may be executed by one or more of blocks 710 and 724 of FIG. 7A, blocks 757 and 765 of FIG. 7B, block 815 of FIG. 8 and block 935 of FIG. 9. In one embodiment, method 1000 is performed by electronic device 100 of FIG. 1, or the motion identification system 200 of FIG. 2.

Referring to FIG. 10, the process begins with measurements of acceleration data being received (block 1005). Measurements are taken according to a sampling rate, which may vary. In one embodiment, the sampling rate may range from one measurement per second to many measurements a second, depending on the operating mode being used.

At processing block 1010, in one embodiment measurements are filtered. Measurements can be filtered to remove high frequency data and/or low frequency data. In one embodiment, what data to filter depends on the type of user activity being detected. At processing block 1012, in one embodiment the inertial sensor is oriented by assigning a dominant axis. Assigning a dominant axis may include calculating rolling averages of acceleration and assigning the dominant axis based on the rolling averages of acceleration. Assigning the dominant axis may also include determining which axis has the largest peak to peak difference. In one embodiment, filtering may simply remove acceleration data not along the dominant axis.

At block 1015, processing logic determines whether a measurement is within a cadence window. If the measurement is not within a cadence window, then no periodic human motion may be recognized or counted for that measurement (block 1040). If the measurement is within the cadence window, the process continues to block 1017.

At block 1017, processing logic determines whether motion criteria are met. For example, in one embodiment the process may determine whether acceleration along the dominant axis is greater than a lower threshold. In one embodiment, the process may determine whether the measurement exceeds the rolling average by a set margin. In one embodiment, processing logic may determine whether acceleration along the dominant axis is greater than previous measurements. Other criteria than those mentioned herein may also be used.

If all required motion criteria are met, then the appropriate periodic human motions are counted (block 1035). In one embodiment, the data from the detected motion is also added to the rolling averages, as described above. Furthermore, as noted above, this process continues while the device is monitoring for periodic human motions.

Figure 11:
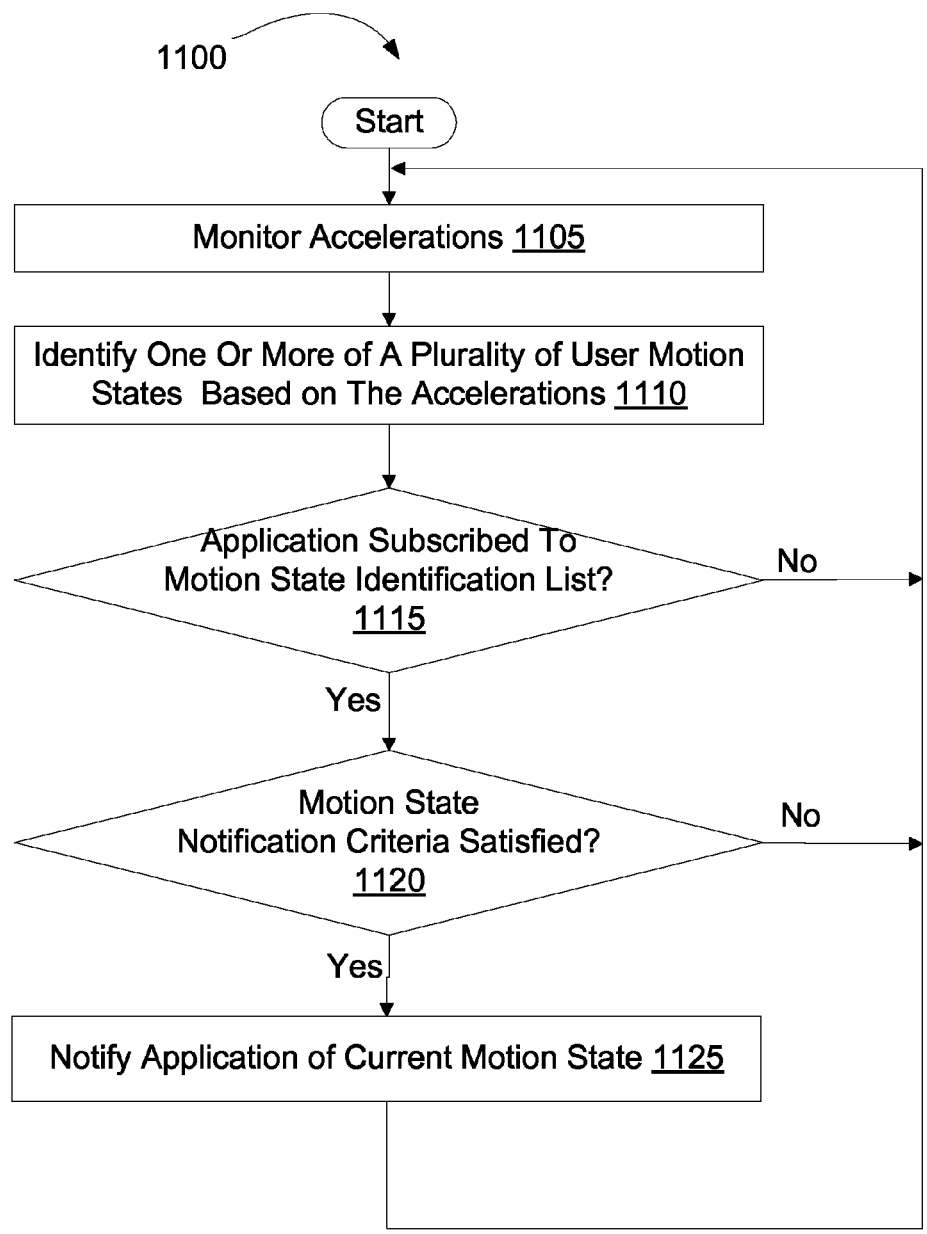
FIG. 11 illustrates a flow diagram for a method of monitoring user motion state using an inertial sensor, in accordance with one embodiment of the present invention.

FIG. 11 illustrates a flow diagram for a method 1100 of determining and utilizing a motion state using an inertial sensor, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 1100 is performed by the electronic device 100 of FIG. 1. In one embodiment, method 1100 is performed by the motion identification system 200 of FIG. 2.

Referring to FIG. 11, method 1100 begins with monitoring accelerations (block 1105). Accelerations may be monitored with an inertial sensor, or other acceleration monitoring device. The monitored acceleration may include filtered and processed acceleration data, as described above. At block 1110, the motion is identified as corresponding to one or more of a plurality of possible motion states based on the accelerations. In one embodiment, a single motion state is identified. In another embodiment, multiple possible motion states are identified, each with an accompanying confidence rating. For example, it may be determined that there is a 90% confidence that a user is walking and a 10% confidence that the user is hopping. The motion states include user activities (e.g. walking, bicycling, inline skating, using an elliptical machine, using a rowing machine, running, hopping, walking up stairs, etc.) as well as non-active motion states (e.g. standing, sitting, riding in a vehicle, being in an elevator, going on an escalator, etc.)

At block 1115, a user motion state identification service subscription list is scanned to determine whether any programs are subscribed to a motion related information service. If one or more programs are subscribed to the service, the method continues to block 1120. Otherwise the method returns to block 1105 to continue monitoring motion states.

At block 1120, entries in the user motion state service subscription list are scanned to determine notification criteria. Examples of notification criteria include, a change in user motion state, a predetermined time interval, etc. If the criteria in an entry are satisfied, the method continues to block 1125. Otherwise the method returns to block 1105.

At block 1125, the program corresponding to the entry in the user motion state subscription list is notified of the identified user motion state. The method then returns to block 1105.

Figure 12:
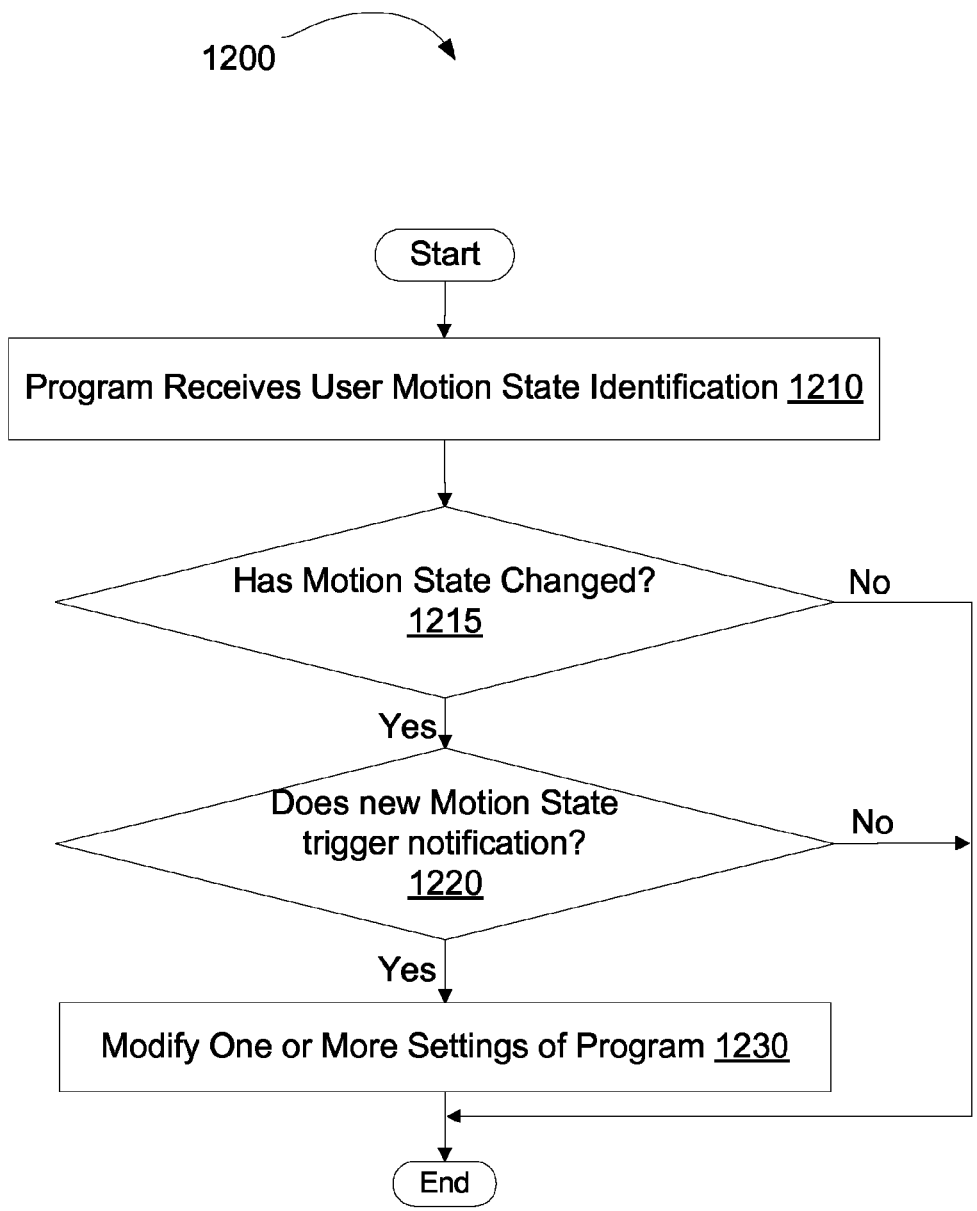
FIG. 12 illustrates a flow diagram for a method of using user motion state related information to modify program settings.

FIG. 12 illustrates a flow diagram for a method 1200 of using motion related information to modify program settings. The method may be performed by processing logic that may comprise hardware (e.g., circuitry, dedicated logic, programmable logic, microcode, etc.), software (such as instructions run on a processing device), or a combination thereof. In one embodiment, method 1200 is performed by the electronic device 100 of FIG. 1. In one embodiment, method 1200 is performed by a program 290 that is coupled to the motion identification system 200 of FIG. 2.

Referring to FIG. 12, method 1200 begins with a program receiving current user motion state information (block 1205). In one embodiment, the program polls a motion identification system and/or a cache to receive the motion state data. In another embodiment, the motion state identification system sends the motion state data to the program without being polled. In one embodiment, the program subscribes to a user motion state identification service or other motion related information service. The motion identification system may send the user motion state identification to all programs that subscribe to the service when predefined conditions are satisfied. For example, the motion identification system may send updates of a current user motion state whenever the current user motion state changes, or may send updates based on other subscription criteria.

In one embodiment, a single user motion state is identified. In another embodiment, multiple different possible user motion states are identified, each with an accompanying confidence rating. For example, it may be determined that there is a 90% confidence that a user is walking and a 10% confidence that the user is riding in a car.

In one embodiment, additional motion related information is received from the motion identification system. For example, the program may receive cadence information, dominant axis information, etc.

At block 1215, the program determines whether the motion state has changed. If the current motion state has not changed, then the method ends. If the current motion state has changed, the method continues to block 1220.

At block 1220, the program determines whether to modify one or more of its settings based on the current motion state. One or more of the settings may also be adjusted based on the additional motion related information. The settings that are modified may depend on the type of program, and the change in motion state. For example, a music application or telephony application may adjust volume based on the identified motion state, a gesture application may alter the motions available, a screen may be turned off, a noise reduction system may be enabled, etc. If the new motion state leads to a change in settings, at block 1230, the appropriate settings are altered in the program. The process then ends. If no change in settings is applicable, the method ends.

Figure 13:
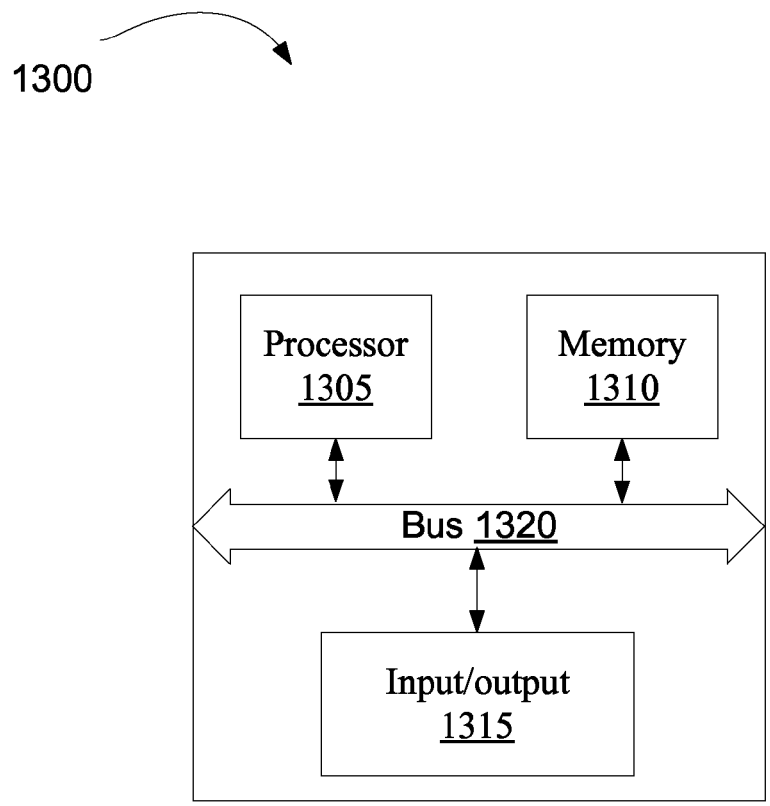
FIG. 13 illustrates a block diagram of a machine in the exemplary form of a computer system within which a set of instructions may be executed in accordance with an embodiment of the present invention.

FIG. 13 illustrates an exemplary block diagram of a specific machine in the exemplary form of a computer system 1300 that may implement the present invention. The exemplary computer system 1300 includes a processing device (processor) 1305, a memory 1310 (e.g., read-only memory (ROM), flash memory, a storage device, a static memory, etc.), and an input/output 1315, which communicate with each other via a bus 1320. Embodiments of the present invention may be performed by the computer system 1300, and/or by additional hardware components (not shown), or may be embodied in machine-executable instructions, which may be used to cause processor 1305, when programmed with the instructions, to perform the method described above. Alternatively, the method may be performed by a combination of hardware and software.

Processor 1305 represents one or more general-purpose processing devices such as a microprocessor, central processing unit, or the like. More particularly, the processor 1305 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 1305 may also be one or more special-purpose processing devices such as an application specific integrated circuit (ASIC), a field programmable gate array (FPGA), a digital signal processor (DSP), network processor, or the like.

The present invention may be provided as a computer program product, or software, that may be stored in memory 1310. Memory 1310 may include a machine-readable medium having stored thereon instructions, which may be used to program exemplary computer system 1300 (or other electronic devices) to perform a process according to the present invention. Other machine-readable mediums which may have instruction stored thereon to program exemplary computer system 1300 (or other electronic devices) include, but are not limited to, floppy diskettes, optical disks, CD- ROMs, and magneto-optical disks, ROMs, RAMs, EPROMs, EEPROMs, magnetic or optical cards, flash memory, or other type of media or machine-readable mediums suitable for storing electronic instructions.

Input/output 1315 may provide communication with additional devices and/or components. In one embodiment, input/output 1315 may transmit data to and receive data from, for example, networked computers, servers, mobile devices, etc. Input/output 1315 may include a screen, speaker, or other mechanism to communicate with the user, as well as buttons, keys, touch sensitive areas or other means of enabling the user to provide input to the device. In one embodiment, the device further includes networking 1320, which enables device to communicate with a server (not shown) or another computer. In one embodiment, the device does not include any user interface features, and the input/output 1315 is designed to interact with a computer system, local or remote, to which the device can be connected. For example, the user may perform configuration and interactions with the device via a web interface, or a local computer program.

In the foregoing description, numerous specific details have been set forth such as examples of specific systems, languages, components, etc. in order to provide a thorough understanding of the present invention. It will be apparent, however, to one skilled in the art that these specific details need not be employed to practice the present invention. In other instances, well known materials or methods have not been described in detail in order to avoid unnecessarily obscuring the present invention. The invention has been described with reference to specific exemplary embodiments. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. An electronic device, comprising:
   a plurality of applications that run on the electronic device;
   an inertial sensor to monitor accelerations experienced by the electronic device; and
   a motion processor comprising;
      a motion state identification system to identify a current motion state based on the accelerations,
      a subscription logic to identify a set of the plurality of applications that subscribe to a motion state identification service, a subscription indicating motion data to be sent to each of the set of applications, and
      the motion processor to notify a subset of the plurality of applications of the current motion state, only when the motion state meets notification criteria associated with the subset of the applications, the notification criteria identified by the subscription logic.

2. The electronic device of claim 1, further comprising:
   the motion state identification system to determine whether the current motion state is different from a previous motion state, and to cause the electronic device to modify one or more settings of the application if the current motion state is different from the previous motion state.

3. The electronic device of claim 1, wherein the current motion state is one of a plurality of potential motion states, the electronic device further comprising:
   the motion state identification system to determine a confidence rating for the current motion state that indicates a probability that the current motion state corresponds to an actual motion state of a present user of the electronic device.

4. The electronic device of claim 1, further comprising:
   the motion state identification system to identify a plurality of potential current motion states, and to identify confidence ratings for each of the identified potential current motion states.

5. The electronic device of claim 1, further comprising:
   the motion state identification system to determine additional motion information from the acceleration measurements, the additional motion information including at least one of a user's current cadence, the user's current rolling averages of accelerations, a current dominant axis, and counted periodic human motion counts.

6. The electronic device of claim 5, further comprising:
   the motion state identification system to identify specific additional motion information the application is configured to receive, and to send the specific additional motion information to the application.

7. The electronic device of claim 1, further comprising:
   the motion state identification system to identify notification criteria associated with the application, and to notify the application of the current motion state when the identified notification criteria are satisfied.

8. The electronic device of claim 1, wherein the motion state identification system notifies the subscribing application of the motion state on a periodic basis, the notification period set by the application.

* * * * *